(12) United States Patent
Möllstam et al.

(10) Patent No.: US 7,981,073 B2
(45) Date of Patent: Jul. 19, 2011

(54) METHOD AND DEVICE FOR IRRIGATION OF BODY CAVITIES

(76) Inventors: Anders Möllstam, Saltsjö Boo (SE); Sven Milton, Vikingstad (SE); Tomas Movin, Huddinge (SE)

( * ) Notice: Subject to any disclaimer, the term of this patent is extended or adjusted under 35 U.S.C. 154(b) by 102 days.

(21) Appl. No.: 11/904,105

(22) Filed: Sep. 26, 2007

(65) Prior Publication Data
US 2008/0243054 A1 Oct. 2, 2008

Related U.S. Application Data

(63) Continuation-in-part of application No. 11/729,357, filed on Mar. 28, 2007.

(30) Foreign Application Priority Data

Mar. 30, 2006 (SE) ...................................... 0600718

(51) Int. Cl.
*A61M 1/00* (2006.01)
(52) U.S. Cl. ................ 604/28; 604/31; 604/67; 604/118
(58) Field of Classification Search .................... 604/27, 604/28, 30, 31, 35, 65, 67, 118, 119; 250/573
See application file for complete search history.

(56) References Cited

U.S. PATENT DOCUMENTS

| 3,979,290 | A | * | 9/1976 | Löffler | ........................... 210/745 |
| 4,998,914 | A | | 3/1991 | Wiest et al. | |
| 5,520,638 | A | | 5/1996 | O'Quinn et al. | |
| 6,175,420 | B1 | * | 1/2001 | Barry et al. | .................... 356/436 |
| 6,396,583 | B1 | * | 5/2002 | Clare | ............... 356/436 |
| 6,517,512 | B1 | * | 2/2003 | Bock et al. | ....................... 604/67 |
| 2003/0236488 | A1 | | 12/2003 | Novak | |
| 2004/0133149 | A1 | * | 7/2004 | Haischmann et al. | .......... 604/31 |
| 2006/0175561 | A1 | * | 8/2006 | Estevadeordal et al. | ....... 250/573 |

FOREIGN PATENT DOCUMENTS

| EP | 0 529 902 A2 | 3/1993 |
| GB | 2 260 622 A | 4/1993 |
| WO | WO86/00534 | 1/1986 |

* cited by examiner

*Primary Examiner* — Kevin C. Sirmons
*Assistant Examiner* — Kami A Bosworth
(74) *Attorney, Agent, or Firm* — Lynn E. Barber

(57) ABSTRACT

A pressure and a vision regulation method and device for irrigation of a body cavity (1), in which an inflow liquid pump (2) pressurizes the irrigation liquid in a feed line (13) and an outflow device (3) or an external suction source (20) drains the irrigation liquid from the body cavity (1) through a tubing (16) into a waste container (17). A control unit (4) controls either the inflow liquid pump (2) only or both the inflow liquid pump (2) and the outflow device (3) depending on an inflow irrigation liquid pressure from a pressure sensor (5). The method and the device are combined with a method for detecting blood cells, red blood cells, haemoglobin and/or debris in liquid coming from a surgical site to provide an automatic control and rinsing system with clear vision in the viewing area of the operational site.

7 Claims, 14 Drawing Sheets

METHOD AND DEVICE FOR IRRIGATION OF BODY CAVITIES

CROSS-REFERENCE TO RELATED APPLICATIONS

This application is a continuation-in-part of copending U.S. patent application Ser. No. 11/729,357 filed Mar. 28, 2007, which claims priority from Swedish application no. 0600718-1 filed Mar. 30, 2006.

TECHNICAL FIELD OF THE INVENTION

This invention relates to the medical field of endoscopic surgery, and in particular the management of liquid that is irrigated into the surgical site during endoscopic procedures.

BACKGROUND OF THE INVENTION

During endoscopic surgical procedures, a surgical site such as a knee joint, shoulder joint or other cavity in the body of a human or animal is viewed with an endoscope. Further in this patent application, the surgical site for an endoscopic procedure is referred to as the body cavity. The body cavity is irrigated with a clear liquid by means of a pump. This pump is further in this patent application referred to as an inflow liquid pump. The clear liquid is as a rule saline, and the pump is usually a peristaltic roller type pump.

Existing liquid management systems are either operated by a fixed flushing volume programmed by the operator of the system when starting the procedure (normally an ml/min value), or by a fixed pressure target for the system. This target pressure is selected by the operator of the system when starting the process. Existing pressure-controlled systems have different ways of measuring the pressure, but the overall technique is to directly or indirectly measure the pressure on the irrigation side of the system. The limitation of the volumetric system is that an excessive liquid volume is needed to achieve a rinsing effect. The limitations with the fixed pressure target systems are firstly that it is impossible to flexibly change the pressure depending on the needs during the operation. Thereby an unnecessary high pressure is used in many cases resulting in tissue swelling and subsequently a risk of tissue damage. Secondly, the fixed pressure controlled systems seldom operate at the fixed pressure target as the systems are based on the measurement of an indirect pressure in the operation site. When the operation site is drained of liquid it takes some time for such a system to react to a lower pressure due to volume/pressure hysteresis of the tissue, and the reaction time can sometimes be very long resulting in an unnecessarily long time of bad visibility during the endoscopic procedure.

With both the volumetric- and the fixed pressure target systems the body cavity expands as a result of the pressure from the irrigation, and the inside of the body cavity can be viewed with an endoscope. The pressure value of the saline solution is an important matter. At a higher pressure, better viewing of the area is accomplished. Also, the pressure holds back blood from vessels that are damaged as a normal effect of the surgical process. Emerging blood obstructs visibility, and it is of course in general desirable to stop bleeding during surgery. The pressure causes tension in the tissue. However, too high a pressure may cause tissue damage, which must be avoided as much as possible. Thus, a precise control of pressure in the body cavity is of vital importance. It is well known how to measure pressure in a liquid, but a direct measuring of pressure in the body cavity is not possible without introducing pressure measuring sensors together with the surgical instruments into the body cavity. However, this method is bulky, expensive and difficult to operate. Alternatively, body cavity pressure can be measured by making an extra perforation of the body for the introduction of a pressure-measuring sensor into the body cavity. The latter makes the surgical procedure more complex, and also causes inconvenience and risk to the patient.

Another problem with endoscopic procedures is that aforementioned blood in the body cavity reduces visibility. Also, the surgical procedures as a rule involve the removal of, or work on tissue, for instance the meniscus of the knee. This results in debris, namely particles of various sizes of tissue floating around in the liquid in the body cavity. This also reduces visibility for the surgeon. These difficulties are routinely managed by rinsing. To rinse out blood or debris, the liquid in the body cavity is replaced by introducing or increasing liquid flow through the body cavity. The pressure may optionally be temporarily elevated. This may stop bleeding as the pressure in the body cavity exceeds that of the blood pressure in the ruptured blood vessels in the body cavity. If the introduction of liquid is made with an inflow liquid pump, the operation is started by pressing a button, or by a foot-operated switch. However, if the outflow of liquid simultaneously is affected, introducing or increasing liquid outflow causes the pressure in the body cavity to drop. If the situation is severe, the flow necessary to rinse the body cavity may have to be very high, and this inevitably causes a significant drop in pressure, and could indirectly be dangerous to the patient as the surgeon is distracted. Furthermore, in some cases the pressure does in fact not drop as a rinse process is initiated. Instead, the body cavity is drained of liquid, but the pressure drops only insignificantly and a pressure regulation function does not foresee that the body cavity is drained. This is due to a high compliance of the body cavity, and in this example this may be the case if the body cavity is a shoulder or a urine bladder. The end result in this case is that the viewing area becomes too small for viewing with the endoscope, but the pressure nearly persists. These repeating obstructions of visibility can be disturbing for the surgeon, and also calls for some action from the user to change pressure, flow or the user may have to wait for quite some time for the situation to stabilize.

DE 3338758, GB 2260622 A, US 2003/0236488 A1, US 2004/0133149 A1, WO 86/00534 and EP 529902 all disclose a method to regulate pressure in an endoscopy system by means of a pressure transducer at the body cavity side of an inflow pump, and a regulating function of the inflow pump. All systems have in common the regulation of pressure of the inflow pump, as the generated pressure is measured by or near it.

In U.S. Pat. No. 5,520,638 a pressure measurement principle is disclosed, using an air filled bladder in the pressurized liquid. The pressurized air transfers the air pressure to a pressure transducer in the inflow pump system. The air filled bladder must be connected to a panel connector via an air line and connector. The major disadvantage of these solutions is that there is a risk of leakage in the air connection to the pump. Such leakage increases the pressure to levels that may endanger the patient, as pressure control is lost. Another disadvantage of these solutions is that the pressure produced by the pump is much higher than in the body cavity as a result of the resistance of flow in the irrigating system. The pressure generated by the inflow pump is controlled by measuring the pressure by the inflow pump itself. The control mechanism in the above mentioned references is a regulating function, where the generated pressure is measured via air filled tubing to a pressure transducer, or by measuring the pressure indirectly by detecting the small expansion of the tubing. The rotational speed of the inflow pump is set to maintain a preferred pressure.

In U.S. Pat. No. 5,556,378, a device is disclosed that measures the pressure difference between a pump irrigating a body cavity, and a suction pump removing liquid from the site. With this system it is complicated, however, to maintain a steady pressure in the body cavity, and two pressure measuring sensors and a complex system are necessary for a desired result. Also, control of flow is basically lost to achieve a desired pressure. This is highly undesirable, as flow should be under control during rinsing procedures, and minimized in between actions of rinsing.

In U.S. Pat. No. 4,998,914 a method to compensate for the conductance of the fluid line is disclosed. This is a way to measure pressure in the body cavity by an indirect method, but the method does not take flow changes into account. Thus, the pressure drop that occurs during a rinsing procedure is not compensated for.

OBJECT OF THE INVENTION

The object of the present invention is to provide for a device and a method for irrigation of body cavities under the independent control of pressure and flow through the cavities.

Another object of the invention is to provide for a device and a method for irrigation of body cavities depending on the detection of blood cells, red blood cells, haemoglobin and/or debris from the surgical site.

The invention enables achievement of control over the pressure in, and flow through, the surgical site, the detection of blood cells, red blood cells, haemoglobin and/or debris from the surgical site, the detection of blood lost from the surgical site, and control of the flow and pressure through the surgical site by use of signals from detectors detecting blood cells, red blood cells, haemoglobin and/or debris from the surgical site.

It also provides for the detection of the pressure in the body cavity without the introduction of instrumentation for pressure measurement.

The object of the invention is also to provide for a process to actively remove the liquid from the body cavity by means of a second pump or other suction source, also usually a peristaltic roller type pump. This process is referred to herein as an outflow device or outflow liquid pump.

SUMMARY OF THE INVENTION

The objects of the invention are achieved by means of the present invention as defined in the accompanying independent claims. Suitable further embodiments will be apparent from the accompanying dependent claims.

The present invention presents a new indirect method to measure pressure in the body cavity such as that of a knee or shoulder during endoscopy procedures. When the body cavity is irrigated, a peristaltic inflow pump generates a pressure; $P_{pump}$. The pressurized liquid is fed via tubing to a viewing instrument such as an endoscope, or another instrument such as a large needle or similar means for irrigation of liquid into the body cavity. Due to resistance in the liquid pathway, there is a loss of pressure. This pressure loss subsists all the way from the inflow pump to the body cavity, and varies by various components forming the liquid path. The pressure loss is higher the smaller the lumen of the liquid pathway is, and the higher the flow is. It is to be noted that the resistance value is not linear with respect to flow. Flow turbulence in the irrigation system causes unlinearities. This is why the resistance of the tubing and instrumentation has to be established by the following method: The resistance values for relevant flow values are established and entered into an electronic memory in the pump system of the invention. This establishment is done in two ways: Initially, at production of the system, the pressures are measured at all relevant flows and input pressures, $P_{pump}$ and pressures in the body cavity, $P_{cavity}$, in a laboratory environment. Thus, a pressure measured at the input of the system corresponds to an achieved pressure in the body cavity. The pressure in the body cavity is measured to establish $P_{cavity}$. This establishment can be made by use of various models for the body cavity such as a knee model, urine bladder model, uterus model etc. The hydrostatic pressure $P_{hyd}$, caused by the difference in height between the pressure transducer and the body cavity should be taken into account. Preferably this should be zero; in other words the calibration is made as the pressure transducer is at the same level as the body cavity. The pressures are noted for each relevant flow step, such as for every 5 ml/min step, and stored permanently in the pump system memory. Several sets of resistance values are established, one for each relevant cassette/tubing/instrumentation setup. If $P_{hyd}$ is 0, the derived resistance, R can be expressed as:

$$R = \frac{P_{pump} - P_{cavity}}{Flow}$$

Secondly, the resistance in the system is reconfirmed during routine use of the system. This reconfirmation is made by a temporary halt of flow by stopping both the inflow and outflow pumps instantaneously. The outflow pump can alternatively be replaced with a valve, which stops the flow in the same manner. This alternative can be used when the liquid management system only operates an irrigation pump. The valve function may comprise means to pinch tubing. At that instant, the pressure is high at the inflow pump, where the pressure is also measured, and lower in the body cavity. The liquid is trapped between the following components: the roller of the inflow peristaltic pump; the cavity of the pressure transducer; the tubing from the pressure transducer to the endoscope connector with shutoff valve; endoscope connector with shutoff valve; the endoscope; the body cavity; the liquid output from the body cavity such as a cannula, shaver or other instrument; the tubing from the output instrument to the rollers of the outflow peristaltic pump, or a valve function; and finally the rollers of the outflow peristaltic pump or a valve function. During the next phase, being approximately 2 seconds, the pressure difference between the inflow pump and the body cavity causes a diminishing flow to the body cavity. If the time the pumps are stopped is long enough, the pressure difference will diminish by a basic rule of communicating vessels. The time constant of this diminishing flow is a representation of resistance. It is to be noted that it is not necessary to hold the pumps stopped for the time it takes for the flow to become zero. An extrapolation of the pressure signal is fulfilling for the purpose of determining an end pressure. This minimizes the time the body cavity is not irrigated. The reconfirmation can be initialized manually by pressing a button, or automatically by regular intervals controlled by the software, or automatically triggered by software if pressure fluctuations occur that indicate that the surgical situation might have influenced resistance.

As mentioned above, the resistance varies with flow, but it does not vary significantly with pressure. The components from the inflow pump to the body cavity basically do not expand as a result of increased pressure. With the described technique of reconfirming resistance, there is little or no flow at the end of the measuring phase, but the inflow tubing and instrumentation are pressurized. If there is a variation in the measured resistance in the inflow system at the same pressure by this method, this is emerging from expansion of the body cavity. In other words, there is a volumetric change. This expansion is pressure dependent and referred to as the compliance. This compliance, C can be expressed as:

$$C = \frac{V_{1cavity} - V_{2cavity}}{P_{1cavity} - P_{2cavity}}$$

The $V_{1cavity}$ is the first volume in the body cavity, and $V_{2cavity}$ is a second volume in the body cavity. $P_{1cavity}$ is a first pressure in the body cavity and $P_{2cavity}$ is a second pressure in the body cavity.

Compliance values can be calculated by the pump system, which measures the pressure as mentioned above, and the flow is proportional to the rotational speed of the roller pump heads. Calculated compliance values are also stored in a memory, and can be used in several ways. One first consideration is the effect the compliance has on the process of reconfirmation of resistance values. The reconfirmation of resistance values is adjusted for as a result of the compliance as the aforementioned time constant is affected by compliance. Another use of the compliance value is to indicate these to the operator. This has the benefit of warning the operator of the risk that excessive liquid may be introduced. The indication can be that of a figure in a display, a "bar indicator" in a display, or a buzzer that emits sound at a predetermined level of compliance. The compliance value can also affect the operation of the pump system by limiting the pressure it produces, to avoid tissue damage.

The above-mentioned flow/pressure relationship is discussed with a constant flow in mind. If one should take not only a constant static flow into account but also the change in flow, the flow restriction in the tubing and instrumentation is described as impedance. Further, and of importance, is the reactive component of the impedance. The reactive component has a restrictive effect on acceleration of the liquid in the tubing and instrumentation. The consequence is that an initiated change of pressure results in a change of flow after some time. At a nominal pressure and nominal flow for an endoscopy system as described, this flow change is approximately 2 seconds. For utmost control of pressure in the body cavity, this reactance must be taken into account. The decision to increase flow is as a rule fairly urgent. Thus, the pressure that accelerates the liquid has to initially be even higher than the designated pressure by the inflow pump to accelerate the liquid. This can be defined as an overpressure. As the flow is to be increased, the reactive component is compensated for by the overpressure. The reactive component has to be established for various instrument setups as well as the resistance mentioned earlier in this patent application. Also, the flow away from the body cavity can optionally be delayed by introducing a delay of the start of the outflow pump to further enhance a rapid increase in pressure. Alternatively, the outflow pump may increase rotational speed with more or less acceleration, as it takes some time to introduce the elevated pressure in the body cavity. Further, if the rinsing is too intense, the inflow may not be able to provide the necessary flow due to the reactance and resistance in the inflow line. It may be necessary to make a decision if the pressure or rinsing has the highest priority, and this can be made by software or by a manual selection by the user. The software decision can be made on a basis of the compliance calculation mentioned above. The manual selection can be a front panel switch with selection of procedure type "knee", "urine bladder" etc.

In yet another situation, the compliance of the body cavity may be very high. In the case of rinsing an irrigated pressurized body cavity, there may be an elevated outflow but the system would not replace the liquid by maintaining the pressure as described above. Pressure would nearly persist, but the liquid volume in the body cavity would drop. Technically speaking, this is a description of tissue hysteresis, originating from the fact that more force is needed from the pressurized liquid to expand tissue surrounding the body cavity than is needed to maintain the body cavity volume. In this particular situation, the viewing field will eventually diminish as the body cavity "caves in". The reason for this is that residual pressure inhibits a relevant inflow to replace the removed liquid. The inflow pump pressure regulation detects a relatively high pressure, as the body cavity is collapsing and the volume drops. When this particular situation is the case, the system may decide to elevate the speed of the inflow pump to that of the outflow pump to compensate for the drawn liquid. The system must however constantly monitor the pressure, as this may not be elevated too high. The above mentioned solution to maintain the viewing area by replacing drawn liquid with the inflow pump with only careful influence of pressure in the body cavity is most beneficial.

In another aspect of the invention, the degree of blood emerging from the body cavity is detected by use of an optical detector. The detector encompasses the fluid path that leaves the body cavity and comprises at least one light emitting diode (LED). At least one photo detector is measuring the light intensity from the LED's that are irradiating the fluid path with light, and this/these incorporate a light sensitive component, such as a light sensitive transistor or light sensitive diode. As known in the art of detecting haemoglobin or red blood cells, the two sensors can measure a baseline by measuring and storing the light surrounding the detector first as the light emitting diode is off. At a rapid interval, the LED is turned on and off at, for instance, a 50% duty cycle. The light detected when the LED is off represents the surrounding light from lamps, the sun etc. The light detected when the LED is on additionally represents the light that has passed through the liquid from the body cavity. The difference between the light measured when the LED is on and when it is off is the signal output from the sensor. This may be derived by use of a microcontroller process to store the aforementioned two signals, and subtracting them. Another solution is to store the two detected signal levels by use of analog circuitry, such as electronic switches and capacitors, or similar sample and hold circuitry as known in this art.

The detector can be haemoglobin sensitive by use of a suitable light wavelength that is haemoglobin sensitive for the first sensor. In a second sensor, a different wavelength is used, and this different wavelength detects the baseline optical opacity of the liquid leaving the body cavity. The comparison of the two sensors results in a signal that is most sensitive to haemoglobin. This comparison is made by subtraction of the two signals from each detector. This subtraction can be derived by use of a microcontroller process to store the aforementioned two signals, and subtracting them. Another solution is to store the two detected signal levels by use of analog circuitry, such as electronic switches and capacitors or similar sample and hold circuitry, and subtracting the two resulting voltages by use of a differential amplifier.

The optical detector is fitted on the housing for the pump system, but may optionally be fitted near or even directly by or within the surgical instrumentation that is forming the liquid path emerging from the patient, such as a shaver or cannula. The advantage of having the detector mounted on the panel of the pump system is that external wiring is not needed, but detachably fitting the optical detector near or even directly by the surgical instrumentation can be accomplished by use of wireless data transfer and a battery operated detector. If the detector is fitted on or within the housing of a shaver, the wiring for the optical detector may be enclosed in the cable for the shaver. The invention can trigger a signal to the operator, if blood is detected.

In another aspect of the invention, the signal values from the blood cells, red blood cells or haemoglobin detection are periodically accumulated in the memory of the processor or in another electronic memory. These accumulated values form a sum of signal values throughout the surgical process. This sum can be multiplied by a calibration factor, and thus be indicative of the amount of blood that has emerged from the patient as a result of the surgical process. This amount of lost blood can be displayed on the instrument display. Furthermore this blood loss can trigger an alarm to the operator, when the detected blood loss has reached a predetermined level.

In another aspect of the invention, the signals from the aforementioned optical sensors are used to detect the absorbance of light of the liquid emerging from the body cavity, as debris originates as a result of the surgical process. This detection is formed by initially detecting and storing the signal from one or both sensors as there is liquid in the optical path. This liquid is clear and thus has a minimum absorbance. This first signal level may be established during a calibration process in conjunction with manufacture, but also in the process of starting up a process of normal use. Having established this first signal, it is constantly compared to the signals from both aforementioned optical sensors during further use of the pump system during a surgical procedure. Furthermore, this debris detection takes advantage of the signal processing of the sensor or sensors as mentioned above in a previous embodiment. The detection of debris is established either from one of the two sensors, or both. The signal from the detector is both that of a rapidly fluctuating signal, as debris is passing by the detector, and an offset with smaller fluctuations representing fine homogenous "milky" substance that appears as a fog when viewed with the endoscope. A signal process detects the intensity of the fluctuations or the depth of absorbance, or both, as indicators of debris in the liquid.

Optionally, a second sensor may be engaged in the inflow system: Anywhere in the liquid path from the source of liquid to the endoscope, the liquid is clear of blood or debris, and may be used as a reference value for detecting blood or debris in the liquid path from the patient.

In an alternative embodiment the optical sensor comprises a video camera and a video signal processor. The video camera can be attached on a surgical instrument or on a separate optical fibre or at the tubing on the outflow site of the surgical site.

The disposable material by the optical detector in the outflow path may be smudged with body fats as a result of the surgical process. The signal processing can compensate for this slow build up of offset of signal from the optical detector.

Rinsing of the body cavity may be initiated manually by the press of a button or a foot operated switch, and results in an increased liquid flow. However the detection of blood or debris may automatically initiate a rinsing process. This detection may in general increase flow through the body cavity and this will beneficially keep the liquid clear. Such increase may be gradual or in steps to achieve the target of a clear viewing filed for the surgeon. Whether decided by a user or automatically by the system, the rinsing of the body cavity can be terminated manually or automatically. Optionally the pressure may be elevated to depress bleeding. This elevation of pressure is preferred as blood is detected, but not debris. Increasing pressure over the patients' perfusion blood pressure reduces the bleeding. The result is that a clear viewing field is maintained automatically and the operator can focus on the endoscopic procedure instead of manually optimizing the liquid management system to give visibility. The operation time will thereby be reduced in most procedures resulting in fewer complications for the patient.

The present invention pressure registration method and the device for irrigation of a body cavity is combined with a method for detecting blood cells, red blood cells, haemoglobin and/or debris in liquid coming from a surgical site so an automatically control and rinsing system is achieved keeping a clear view in the viewing area of the operational site.

BRIEF DESCRIPTION OF THE DRAWINGS

FIG. 2a indicates a first embodiment of an outflow device.
FIG. 2b indicates a second embodiment of an outflow device.
FIG. 2c indicates a third embodiment of an outflow device.

DETAILED DESCRIPTION OF THE INVENTION

Figure 1:
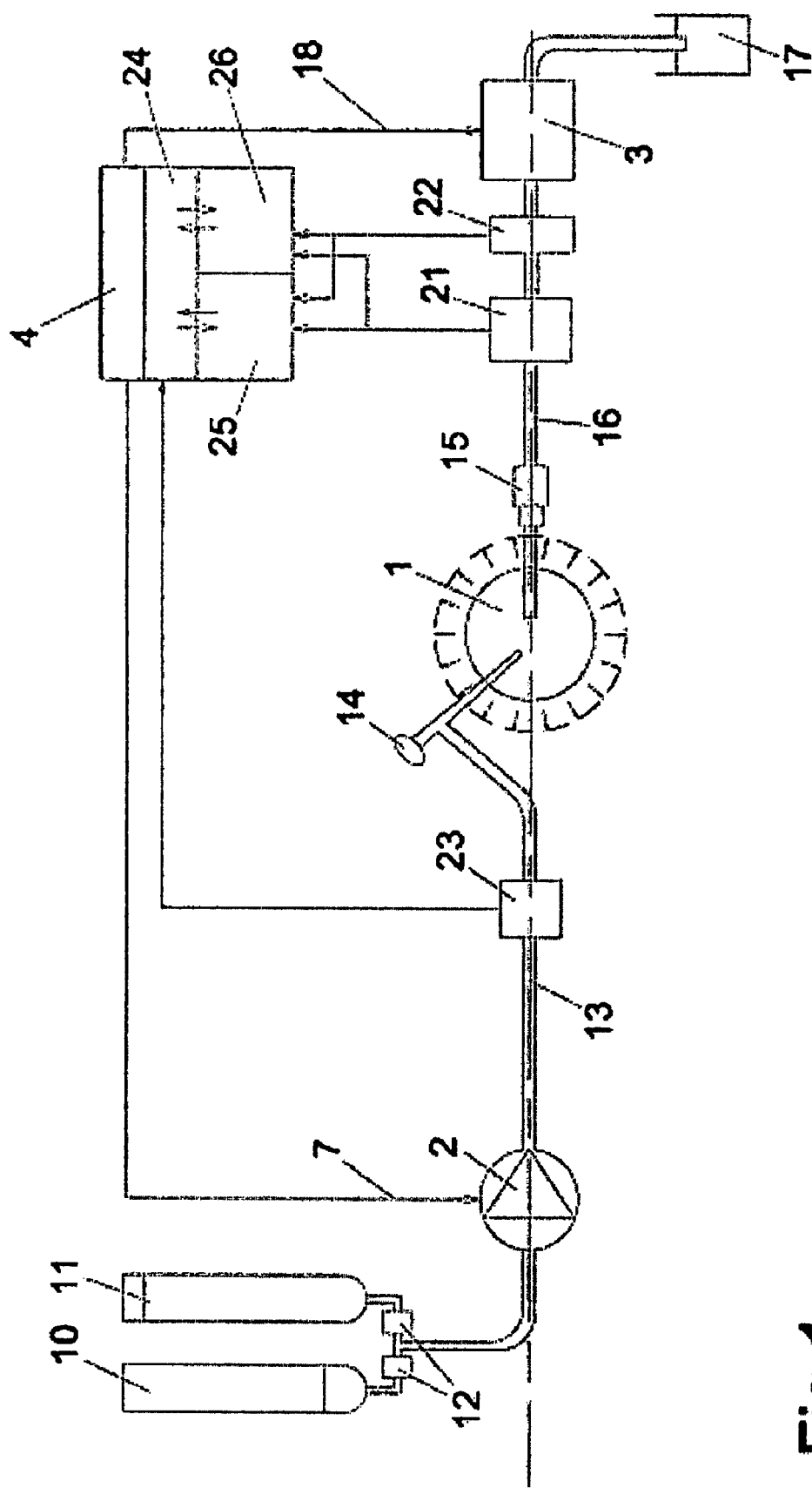
FIG. 1 shows a first feature of the invention.

When a body cavity is irrigated, a peristaltic inflow pump generates a pressure. Due to resistance in the liquid pathway, there is a loss of pressure along it. This pressure loss subsists all the way from the inflow pump to the body cavity, and varies by various components forming the liquid path. The higher the flow, the higher the resistance. This resistance is not linear with respect to flow. At the design of an irrigation system, the resistance values for relevant flow values are to be established in a laboratory environment. Thus, a pressure measured at the input of the system corresponds to an achieved pressure in the body cavity. Then the measured "actual" values for the pressures in the body cavity can be calculated from the flow and the established resistance.

The method to establish the pressure in the body cavity without measuring pressure in it is further enhanced in the following way: When there is a need for a change in flow or pressure, the acceleration of the liquid is firmly enforced by over pressure from the inflow pump. In that fashion, the inductive (reactive) components of the liquid path are accounted and compensated for. The end result is a control over pressure in the body cavity that overcomes the resistance and reactance in all aspects in the liquid flow path.

The pump system controls the flow by the rotational speed of two roller pumps. Both the irrigation liquid and the liquid that is extracted from the body cavity are individually controlled. The invented irrigation system keeps track of liquid administration by memorizing the number of turns the inflow and outflow roller pumps are completing. A difference in inflow and outflow of liquid indicates how much liquid is introduced into the body cavity and its surroundings. Should the pump system deliver a higher inflow than outflow, pressure in the body cavity is increasing. By analyzing the pressure and flow, the compliance can be calculated. Also, the amount of liquid that leaves the body cavity can be calculated. This is done in the following way: With a stabilized pressure, nominally, there is no liquid loss. If liquid leaves the body cavity, the inflow pump needs to make more turns than the outflow pump to maintain a constant pressure. A slow or minor increase in such liquid loss indicates that the liquid is leaving the surgical site, but stays within the immediate surroundings of the surgical site. The difference in number of rotational turns the pump heads complete represents such lost liquid volume. The pump system can record and/or alarm when predetermined values of liquid are leaving the body cavity into tissue surrounding the body cavity or are leaking out from the surgical site through any of the ports used for instruments. It is highly beneficial to the user to get an indication of leakage. The leakage out from the operational site is visible for the operator but leakage into tissue is normally difficult to detect. If above mentioned liquid loss is increasing very rapidly, it is indicative of a mechanical or technical circumstance, such as a leakage in a connector, and should not be inclusive in the calculated amount of liquid introduced into the body. At such stage of liquid loss, the pump may stop and/or give an alarm.

During an endoscopy procedure, it will periodically be necessary to rinse the body cavity from blood and debris. This is basically done by initiating or increasing flow through the body cavity.

To furthermore secure pressure and flow control, the pump system outflow pump follows that of the inflow pump during a rinse procedure. Shortly after flow is increased, as described above, the outflow pump follows the same rotational speed as the inflow pump, relevant for the new desired elevated flow. The system must however constantly monitor the pressure, as described above, as this may not be elevated too high. In many cases of endoscopic surgery this solution to maintain the viewing area by immediate replacement of drawn liquid with the inflow pump irrespective of pressure in the body cavity is most beneficial.

FIG. 1 shows a first feature of the invention as a pump system for use in irrigating a body cavity 1 which pump system comprises an inflow liquid pump 2, an outflow device 3 and a first control unit 4 containing electronics with a microcontroller for the drive of the pumps, memory circuits including a calculating function unit, front panel, power supply etc. Also, a pressure sensor can be electrically connected to the first control unit by a signal line through which an electric signal corresponding to the actual liquid pressure is delivered to the control unit, (not indicated in FIG. 1). The first control unit 4 is also electrically connected to the inflow liquid pump 2 by an input pump signal line 7. The pump system withdraws saline from a first container 10 by means of the pump of the inflow liquid pump 2, preferably being a peristaltic roller pump. The first container 10 may cooperate with a second container 11 by means of at least one container valve 12. The container may consist of one or two glass bottles or plastic bag containers. Thus, a second container can quickly be selected as the first one is consumed by switching the container valve/valves 12. The pump system pressurizes the body cavity, which can be a knee, a shoulder, an elbow, a hip, a hand or a foot, via a feed line 13 and via an endoscope 14. There is a pressure drop over the feed line 13 and most particularly at the inlet and through the passage of the endoscope 14. The outflow device 3 can be an outflow liquid pump, an outflow shut off valve or a combination of an outflow shut off valve and an external suction source. In case the outflow device is a liquid pump, preferably of a peristaltic roller type, it removes the liquid via an instrument such as a shaver 15 or similar type of instrument. The latter may be a cannula. The liquid is further withdrawn by the outflow device 3 through a tubing 16 into a waste container 17. Furthermore, the first control unit 4 is electrically connected to the outflow device 3 by an output device signal line 18.

The liquid coming out from the operating site through tubing 16 has been provided with a first optical sensor 21 arranged with a suitable wavelength adopted to identify blood cells, red blood cells, haemoglobin in the liquid coming out from the operating site through the tubing 16 and to give electrical signals to a second control unit 24, a clear vision module, indicating the actual amount of blood cells, red blood cells, haemoglobin in the liquid coming out from the operating site. The resulting automatic or manual action taken is an increase flow level at constant pressure for reducing the sight problem or an increase of the pressure level at constant flow level to stop bleeding or both.

The tubing 16 is also provided with a second optical sensor 22 to identify debris in the liquid coming out from the operating site through tubing 16 and to give electrical signals to the second control unit 24 indicating that there is debris in the liquid coming out from the operating site. Both the first optical sensor 21 and the second optical sensor 22 can be combined into the same housing. The sensors both send visibility signals to the clear vision module 24 in order to be correlated to a clear vision reference in the module and to regulate the flow values through the body cavity during the surgical procedures. Also a separate debris identification module 25, indicating debris in the liquid coming out from the operating site is provided for cooperation with one or both of the sensors 21, 22 and the second control unit 24, the clear vision module. Furthermore, a separate blood amount detector module 26 indicating the actual amount of blood cells, red blood cells, haemoglobin in the liquid coming out from the operating site is provided for cooperation with one or both of the sensors 21, 22 and the second control unit 24, the clear vision module. The interaction between the debris identification module 25, the blood amount detection module 26 and the second control unit 24 is indicated with double arrows. A third optical sensor 23 may be attached to the feed line 13 for calibration purposes of the first and second optical sensors as the saline solution in the feed line is crystal clear.

Note that the optical detectors 21, 22 may be fitted by the shaver 15 or similar instrument. This would further reduce the response time of the detection of blood and debris. Note also that the outflow device 3 is not necessary for the function of the clear vision purposes of FIG. 1. Furthermore, operating devices such as buttons, foot pedal and a remote device together with presentation devices are also provided but are not indicated in the figure.

Figure 2:
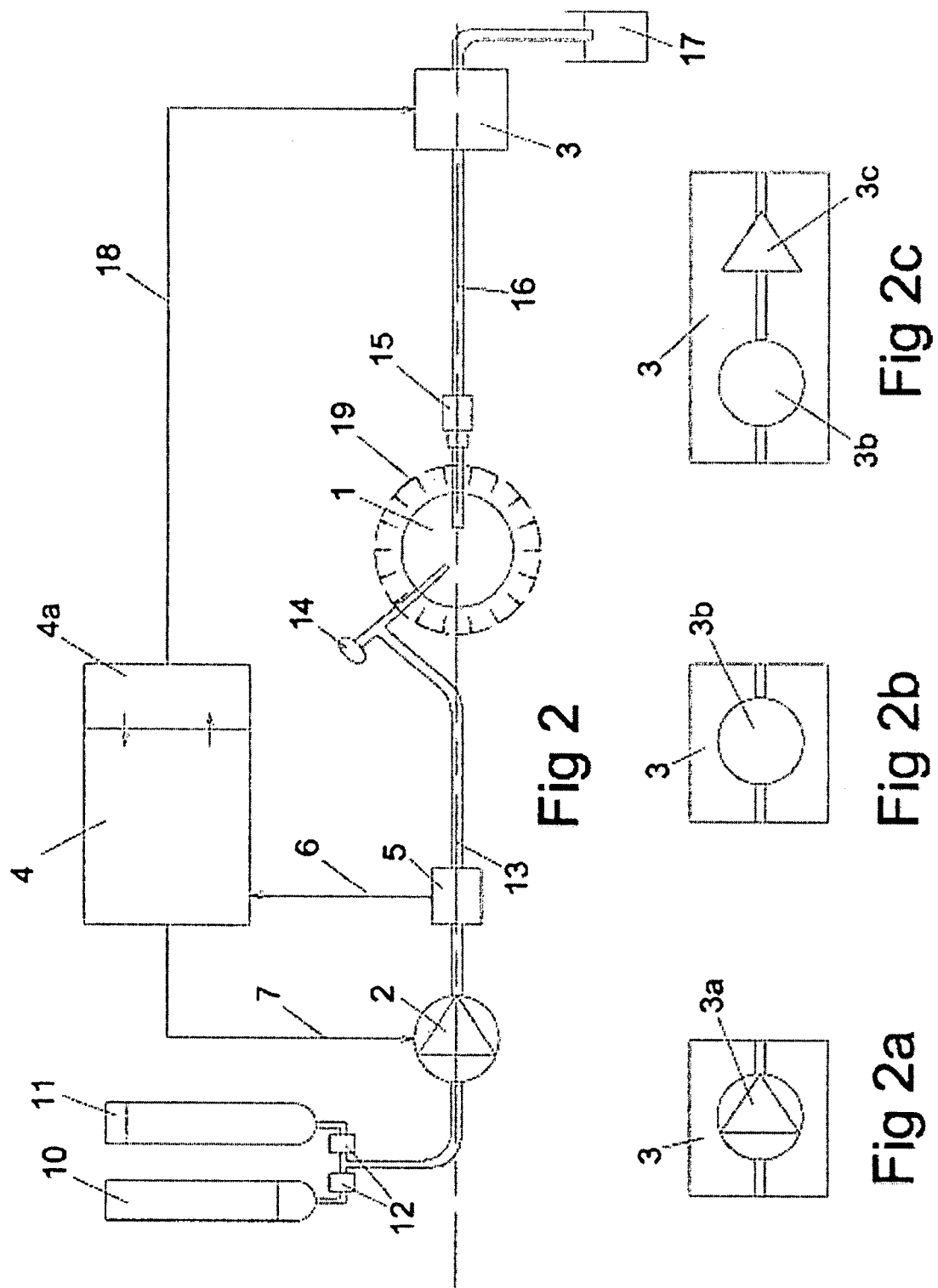
FIG. 2 shows a second feature of the invention.

FIG. 2 shows a basic configuration of a pump system for use in irrigating a body cavity 1 which pump system comprises an inflow liquid pump 2, an outflow device 3 and a first control unit 4 containing electronics with microcontroller for the drive of the pump heads, memory circuits including a calculating function unit 4a, front panel, power supply etc. The calculating function unit 4a serves as a reference for a feed back control system, indicated by the two arrows between the first control unit 4 and the calculating function unit 4a, in achieving real pressure values in the body cavity 1. The calculating function unit 4a compares the inflow irrigation liquid pressure and flow with pressures calculated to correspond to pressures in the body cavity 1 for the respective flow for a nominal surgical site. A pressure sensor 5 is electrically connected to the first control unit 4 by a signal line 6 through which an electric signal corresponding to the actual liquid pressure is delivered to the control unit. The first control unit 4 is also electrically connected to the inflow liquid pump 2 by an input pump signal line 7. The pump system withdraws saline from a first container 10 by means of the pump head of the inflow liquid pump 2, preferably being a peristaltic roller pump. The first container 10 may cooperate with a second container 11 by means of at least one container valve 12. The container may consist of one or two glass bottles or plastic bag containers. Thus, a second container can quickly be selected as the first one is consumed by switching the container valve/valves 12. The pump system pressurizes the body cavity, which can be a knee, a shoulder, an elbow, a hip, a hand or a foot, via a feed line 13 and via an endoscope 14. There is a pressure drop over the feed line 13 and most particularly at the inlet and through the passage of the endoscope 14. The outflow device 3, preferably of a peristaltic roller type, removes the liquid via an instrument such as a shaver 15 or similarly type of instrument. The latter may be a cannula. The liquid is further withdrawn by the outflow device 3 through a tubing 16 into a waste container 17. Furthermore, the first control unit 4 is electrically connected to the outflow device 3 by an output device signal line 18.

As is indicated in FIGS. 2a, 2b and 2c the outflow device is provided with three separate embodiments. In FIG. 2a the outflow device is an outflow liquid pump 3a. In FIG. 2b the outflow device is an outflow shut off valve 3b and in FIG. 2c the outflow device is a combination of an outflow shut off valve 3b and an external suction source 3c.

This basic configuration of a pump system makes it possible to maintain a pressure regulation in the body cavity in that the pressure sensor 5 indicates the actual pressure in the feed line 13, which actual pressure is compared to memorized pressure values in a static part of the calculating function unit 4a which actual pressure values correspond to empirical acquired real values in a table of a nominal body cavity, or calculated values. By the use of such calculating function unit 4a it is possible to obtain a constant actual pressure regulation in the body cavity in that the first control unit 4 also regulates the outflow liquid pump 3a. An increased flow value through the body cavity at constant pressure can be maintained by an increased speed of both the inflow liquid pump 2 and the outflow liquid pump 3a. An increased pressure value in the body cavity at constant flow can be maintained by an increased speed of the inflow liquid pump 2 holding the outflow liquid pump 3a at a constant speed. The surgical site of the body cavity will then expand as indicated by the arrows in FIG. 2 to an enlarged body cavity volume 19. This constant pressure control in the body cavity can be maintained automatically by the system when a change in liquid flow is initiated. Also a constant pressure control in the body cavity can be maintained automatically at an altered level by the system without a change of liquid flow through the body cavity.

A second part of this basic configuration of the pump system makes it possible to alter the function to compare the inflow irrigation liquid pressure and flow with pressures calculated to correspond to pressures in the body cavity for the respective flow for a nominal surgical site in order to work for a body cavity that does not follow the nominal default values. This is made as previously described in the following way by stopping both the inflow and outflow pumps 2, 3a instantaneously and then measuring the pressure difference during approximately two seconds in the trapped liquid volume between the inflow and outflow pumps 2,3a. It is to be noted that the invention is not limited to systems with an outflow pump. The outflow pump can alternatively be a shut off valve 3b. After this time period the measured pressure values can be mathematically extrapolated to the end pressure in the body cavity 1 and thus making up new values for an actual body cavity.

Figure 3:
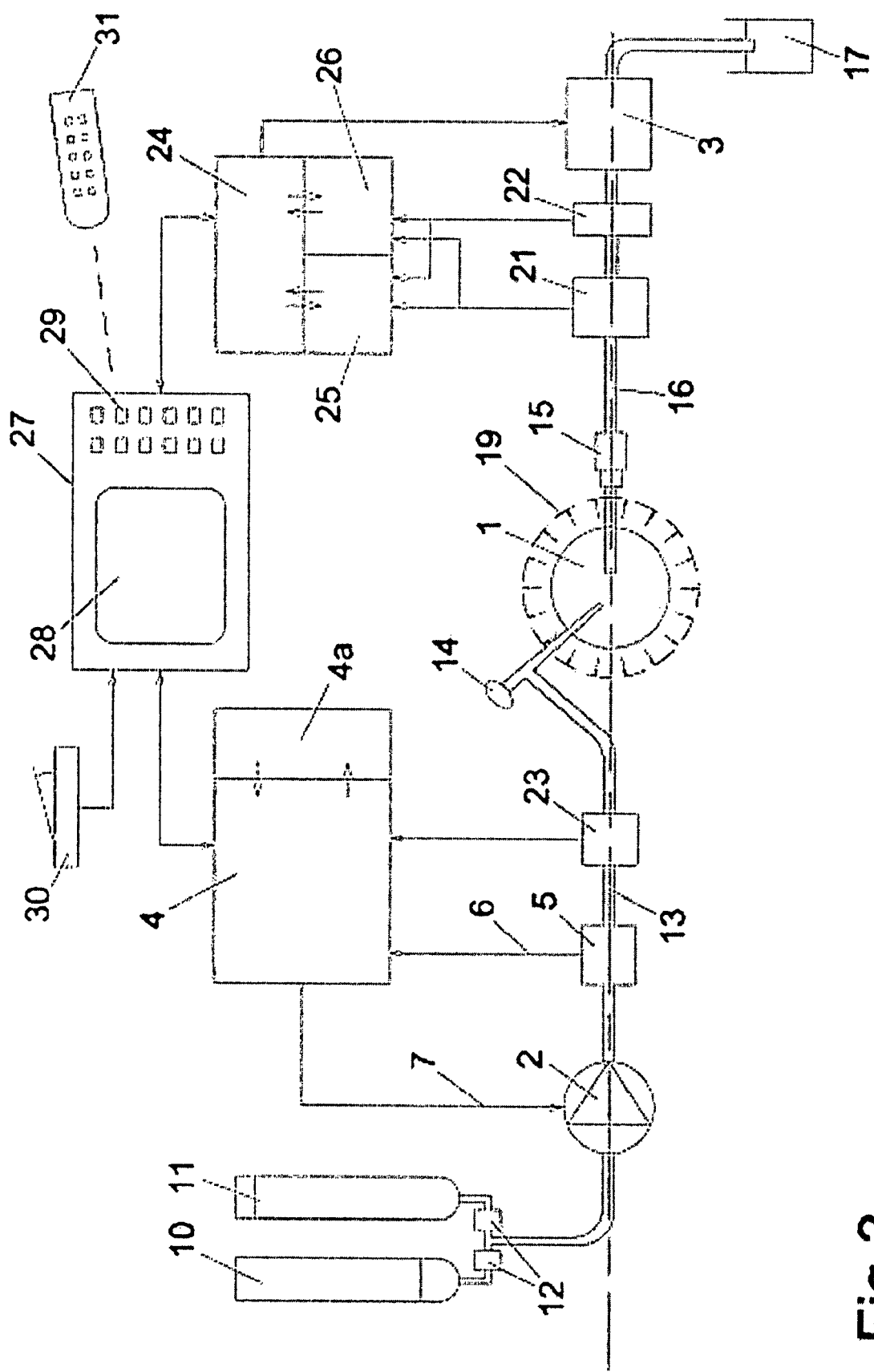
FIG. 3 shows a third feature of the invention.

FIG. 3 shows an alternative configuration of the invention where identical parts from FIGS. 1 and 2 have the same reference numbers. In addition to the basic configuration in FIG. 2 the area where liquid is coming out from the operating site through tubing 16 has been provided with a first optical sensor 21 arranged with a suitable wavelength adopted to identify blood cells, red blood cells, and haemoglobin in the liquid coming out from the operating site through the tubing 16 and to give electrical signals to a second control unit 24, a clear vision module, indicating the actual amount of blood cells, red blood cells, and haemoglobin in the liquid coming out from the operating site. The resulting automatic or manual action taken is an increased flow level at constant pressure for reducing the sight problem or an increase of the pressure level at constant flow level to stop bleeding or both.

The tubing 16 is also provided with a second optical sensor 22 arranged with another wavelength adopted to identify debris in the liquid coming out from the operating site through tubing 16 and to give electrical signals to the second control unit 24 indicating the actual amount of debris in the liquid coming out from the operating site. Both the first optical sensor 21 and the second optical sensor 22 can be combined into the same housing. They both send vision signals to the clear vision module 24 in order to be correlated to a pressure control in the module and to regulate the flow values through the body cavity during the surgical procedures as previously described. Also a separate debris identification module 25, indicating the amount of debris in the liquid coming out from the operating site, is provided for cooperation with one or both of the sensors 21, 22 and the second control unit 24, the clear vision module. Furthermore, a separate blood amount detector module 26 indicating the actual amount of blood cells, red blood cells, and haemoglobin in the liquid coming out from the operating site is provided for cooperation with one or both of the sensors 21, 22 and the second control unit 24, the clear vision module. The interaction between the debris identification module 25, the blood amount detection module 26 and the second control unit 24 is indicated with double arrows.

Note that the optical detectors 21, 22 may be fitted by the shaver 15 or similar instrument. This would further reduce the response time of the detection of blood and debris.

A third optical sensor 23 may be attached to the feed line 13 for calibration purposes of the first and second optical sensors as the saline in the feed line is crystal clear.

FIG. 3 also shows an operating control device 27 with a display 28 for presentation of the surgical area inside the body cavity and the various values for control over the surgical procedure. Operating devices such as buttons 29, foot pedal 30 and a remote device 31 are provided for the surgeon to alter flow, pressure, change levels of parameters, chose presetting of cavity type, service mode, alarms, etc. As can be seen in the figure the operating control device 27 operates both the first control unit 4 and the second control unit 24. Similar operating devices are also provided in the basic configuration of the pump system according to FIG. 1.

Figure 4:
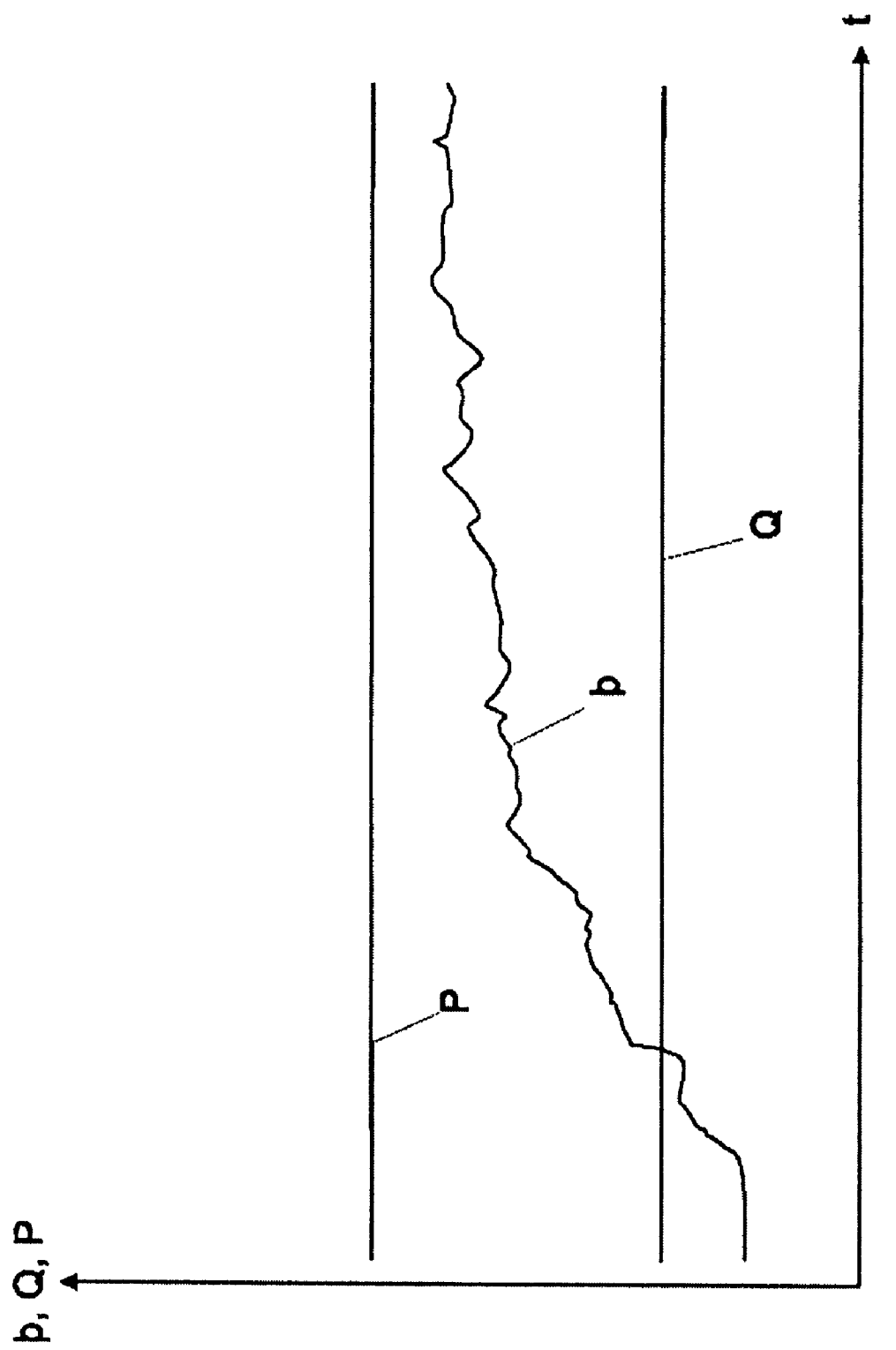
FIG. 4 shows an initial time diagram with optical sensing.

In FIG. 4, a time diagram describes the situation when blood or debris is emerging and increasing from the surgical site. The pump system comprises means to automatically increase flow through the surgical site, should blood or debris be detected. In this figure, the automated increase is not engaged. The curve P shows the pressure in the surgical site, and the flow curve Q represents the liquid flow through the surgical site. Both curves show constant values. The voltage signals from the optical sensors 21, 22 (in FIGS. 1 and 3) represents an optical density curve þindicating increasing optical density from blood and/or debris. This would be the situation as more and more blood and/or debris is withdrawn from the surgical site. This is in all indicative of too much blood and/or debris in the surgical site, severely reducing visibility to the surgeon.

Figure 5:
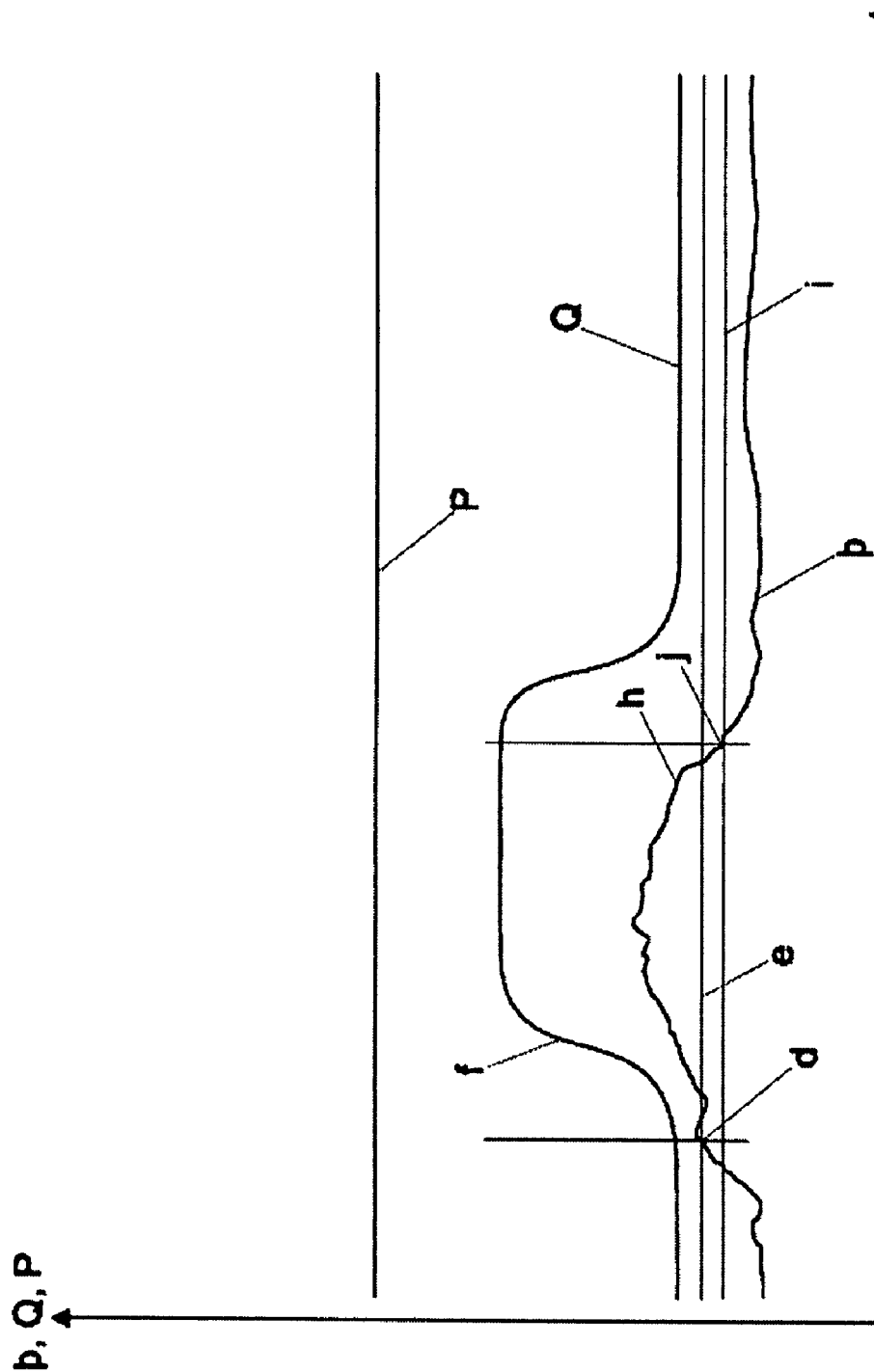
FIG. 5 shows a compensating debris time diagram according to FIG. 4.

In FIG. 5, a time diagram describes the situation when debris is emerging from the surgical site. The automated increase of flow when emerging debris is detected is now engaged. The pressure curve P shows a constant pressure which indicates that a constant pressure algorithm is active while the flow curve Q shows an increased flow. The voltage signals from the second optical sensor 22 (in FIGS. 1 and 3) representing an optical density curve þindicates an increasing degree of blood and/or debris. At the time at d the voltage signal from the optical sensor is strong enough to indicate a disturbing amount of debris, and a first density trigger level e is reached. This trigger level is set at the manufacturing of the pump system, but may be adjusted by technical personnel if found necessary. This triggering appoints to the inflow and outflow pumps to elevate flow through the surgical site. This elevation of flow is shown at f on the flow curve Q. The pressure may optionally be elevated at this stage to eliminate bleeding at the surgical site. This elevation is part of the pressure regulating mechanism of the pump system, and is achieved by letting the inflow pump run faster than the outflow pump for the time necessary to elevate pressure. The elevated flow rinses the surgical site, so the optical density from debris will as a result fade as is shown at h. When the optical density has reached a second density trigger level i, at the time j, the increased flow can be normalized again, and the pressure—if elevated—may be also be normalized again, as the automated rinse process is finished.

Figure 6:
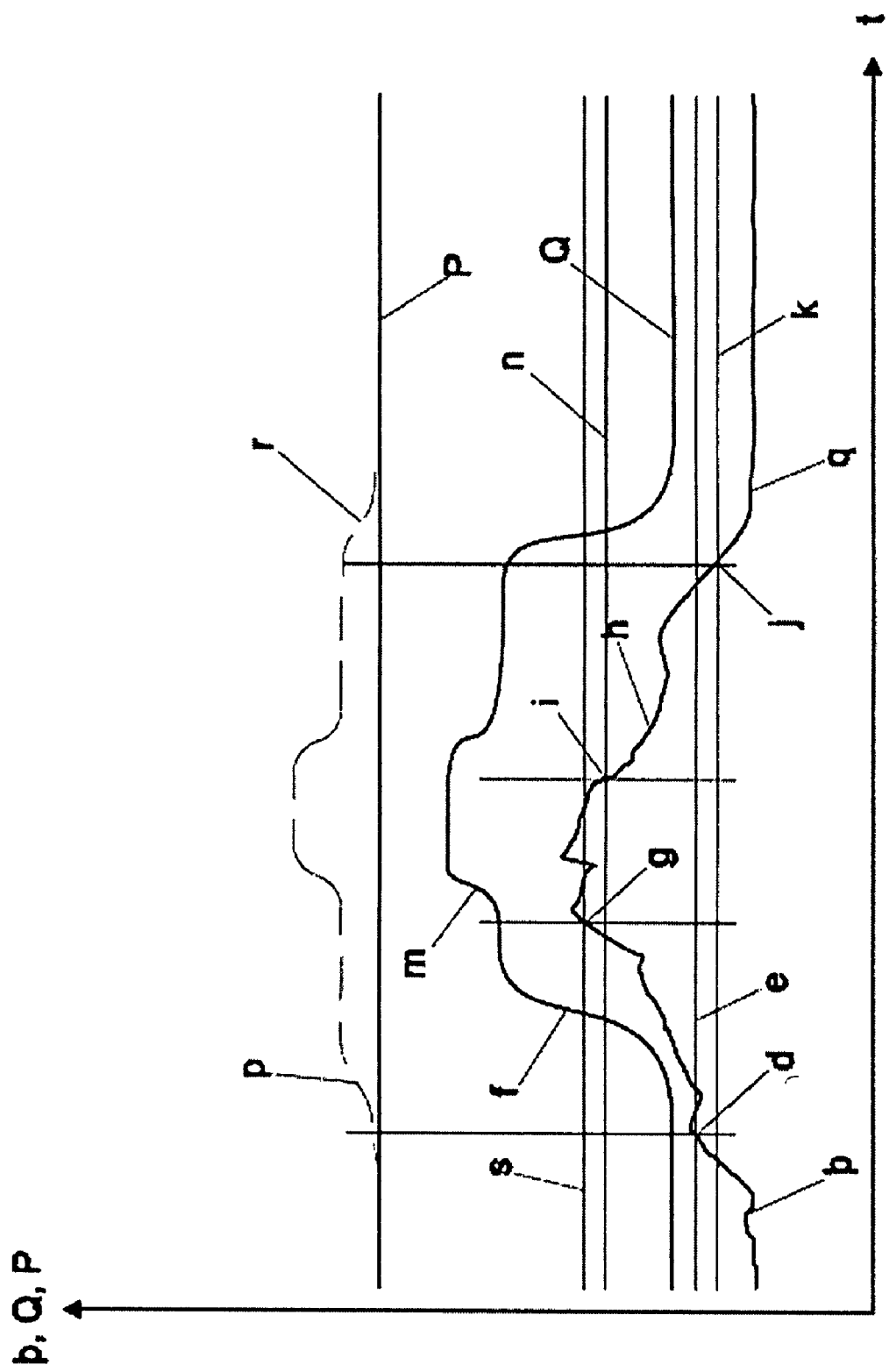
FIG. 6 shows a compensating red blood cells time diagram according to FIG. 4.

In FIG. 6, a time diagram over red blood cell detection describes the situation when a loss of blood from the surgical site is high. The automated increase of flow when emerging blood is detected is engaged. Again, the pressure curve is indicated by P, and the flow curve is indicated by Q. The voltage signals from the first optical sensor 21 (in FIGS. 1 and 3) represent an optical density curve þindicating an increasing degree of blood. At the time d the voltage signal from the optical sensor is strong enough to indicate a disturbing amount of blood, as a first density trigger level e is reached. This appoints to the inflow and outflow pumps to elevate flow through the surgical site. This elevation of flow is shown at f on the flow curve Q. The pressure may optionally elevate at this stage indicated by p on the dotted part of the pressure curve P. As the degree of blood is severe, the optical density increases further so the signal voltage reaches a second density trigger level s at the time indicated by g. The flow is now elevated even higher as shown by the Flow curve Q at m. This results in sufficient rinsing of the surgical site. Now, the optical density will reduce and reach a third density trigger level n at the time i. The amount of blood is further reduced at the flange h on the optical density curve þ. At the time j the optical density is reduced to a fourth density trigger level k which at last represents a normal situation with no or little blood. The increased flow can be normalized again, and the pressure—if elevated—may also be normalized again as indicated at r, as the automated rinse process is finished.

In detecting blood cells, red blood cells, and haemoglobin during a time interval and knowing the flow during this interval an indication of blood loss is established and registered by the blood amount detector module 26 which is valuable information to the surgeon.

Figure 7:
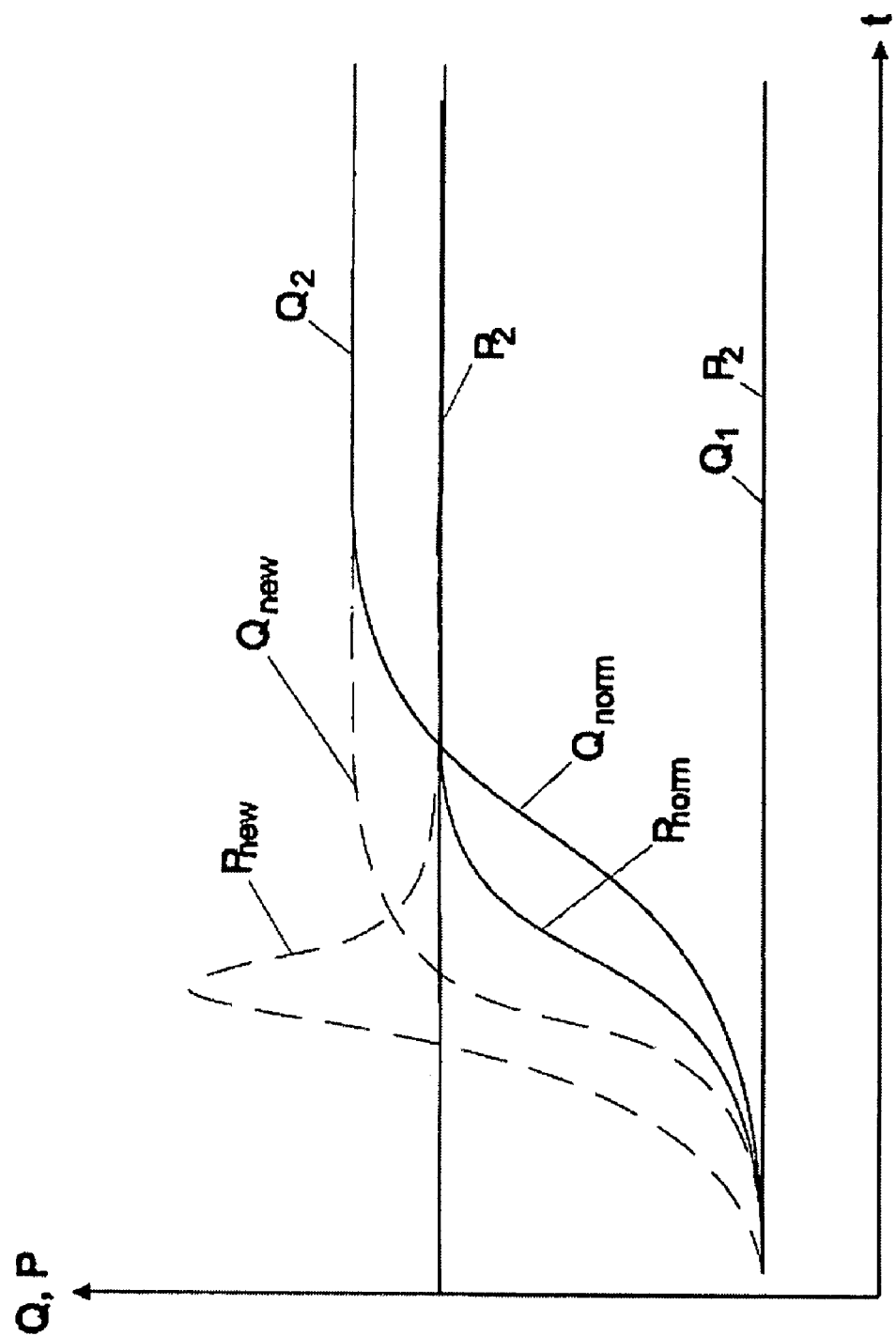
FIG. 7 shows an initiating flow and pressure diagram.

In FIG. 7 a situation is described when the flow Q is to be increased from a low flow value Q1 to a high flow value Q2 in the liquid path. The pressure P is increased from P1 to P2 as described in the timing diagram. The pressure curve $P_{new}$ describes a normal increase of pressure, resulting in a normal increase of flow as shown in the flow curve $Q_{norm}$. However, in the present invention, the pressure is rapidly elevated to a pressure far above the new pressure level $P_2$ and down to the pressure level of $P_2$ as described with pressure curve $P_{new}$, resulting in a much quicker flow response indicated by the flow curve $Q_{new}$.

Example 1

Smart Vision/LED

Below is an example of a technique to detect and distinguish blood and debris in the liquid that is aspirated from a knee joint during an arthroscopic procedure while using an irrigation system for body cavities. Signals from this detection is used to control the pressure in, and liquid flow through the knee joint in a manner that keeps it clear from blood and debris for good viewing with the arthroscope. If debris is detected, the flow through the knee joint is automatically elevated to efficiently rinse it. If blood is detected, the pressure is also automatically elevated, to inhibit blood from leaving the broken vessels, by overcoming the blood pressure.

Work is performed in the knee with surgical tools such as forceps, scissors, rotating burrs and drills. Various forceps are used to detach tissue, and as a result some of this tissue will float in the liquid in the surgical site. These particles of tissue may be of bone, cartilage, small tissue fragments or very small tissue fragments that appear as a milky substance. As a result of all of these surgical activities, all tissues of various sizes have to be removed from the surgical site. Another effect is that blood may emerge from broken blood vessels. Both tissue particles and fragments, referred to as debris, and blood diminish view and must be removed.

The system removes the liquid from the surgical site by means of an aspiration pump. The intrinsic flow is 150 ml/min. The pump is a peristaltic roller type pump known in the art of pumping liquids. The pump is stepper motor driven model SR 25, available from ASF Thomas, Industries GmbH, Siemensstrasse, 82178 Puchheim, Germany, and has a flow range of 0-740 ml/minute.

Figure 8:
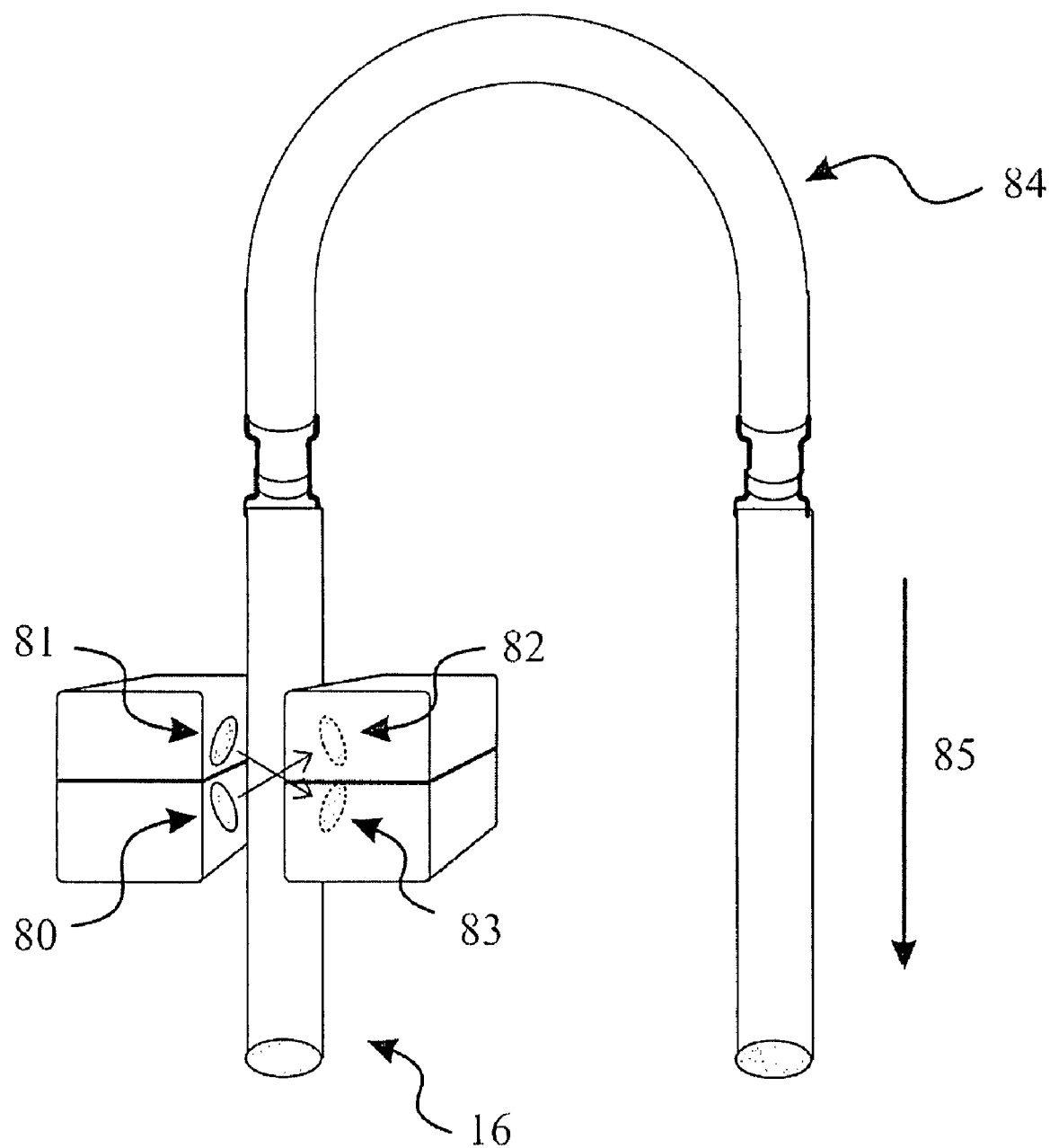
FIG. 8 shows the optical sensor arrangement

The removed liquid thus consists of the irrigated liquid, body fluids present in the joint, and, if developed, debris or blood or both. Tubing from the surgical site forms the pathway of aspirated liquid from an outflow cannula fitted in the joint as an outflow port to a light irrigation and detection arrangement shown in FIG. 8. Two light emitting diodes (LED)'s (80) (Model L200CUV395-12D UV from LEDtronics Inc, sold by ELFA AB, Elektronikhojden 14, Jarfalla, Sweden and 81-Model L2791-02 from Hamamatsu, also sold by ELFA AB, Elektronikhojden 14, Jarfalla, Sweden) emit two wavelengths of light through a transparent vessel in the outflow tubing (16). Liquid flow is achieved with the outflow pump that has a peristaltic roller pump with tubing (84) generating a flow (85). Two photo detectors (82, 83 both Model OP905 from Optek, sold by ELFA AB, Elektronikhojden 14, Jarfalla, Sweden) are measuring the light intensities from the LED's that are irradiating the fluid path; one for each LED. The LED (80)/photodetector (82) combination form optical sensor 21 in FIG. 1. The LED (81)/photodetector (83) combination form optical sensor 22 in FIG. 1. The light paths from each LED/photo detector pair coincides in a common sample volume in the vessel. Signals from the photo detectors are amplified with adjustable amplification factors that adjust the signal levels to suit the inputs of A/D converters and make calculations possible by a microcontroller in the system. First, the two photo detectors measure a background light intensity by measuring the light surrounding the detector while the light emitting diodes are off. These values are stored by the microcontroller. The light detected when the LEDs are off represents the surrounding light from lamps, the sun etc. At an interval of 10 Hz, the LED is turned on and off at a 50% duty cycle. The light detected when the LED is off represents the surrounding light from lamps, the sun etc. The light detected when the LED is on additionally represents the light that has passed through the liquid from the body cavity. The difference between the light measured when the LED is on and when it is off is the signal output from the sensor comprising the photo detector, analog amplifier and A/D converter. The output signal value from the sensor system is derived by use of a microcontroller process to store the aforementioned two signals, and subtracting them.

The detection of hemoglobin is obtained by use of a light wavelength that is hemoglobin sensitive, namely 370 nm, for the first LED (80). The second LED (81), has a wavelength of 875 nm, and this is detecting the baseline optical opacity of the liquid compound leaving the body cavity. The comparison of the two signals results in a signal that is most sensitive to hemoglobin. This comparison is made by subtraction of the two signals from each detector. This subtraction is made by the system microcontroller, which stores the aforementioned two signals, and subtracts them. The result is a Hb (Hemoglobin) signal that range from 10-50% of the baseline Hb signal; baseline meaning that no Hb is present. When the signal level is elevated 20% over the baseline, the system concludes that blood is present in the vessel by the photo detectors. The amplification of the Hb signals is to be calibrated by use of human blood in a calibration environment. A second Hb signal level of 40% indicates that a significant amount of blood is present.

As a predetermined level of blood is reached, the system identifies the situation and will react by increasing the flow of the aspiration pump to a higher level to rinse the knee. This higher level is preselected in the menu of the pump system, and is in this case 300 ml/min. If a significant amount of blood is present, the flow will increase to 450 ml/min. When the blood detection determines that the increased flow has rinsed the knee as the signal level has returned to a low level, the aspiration pump will return to the intrinsic flow of 150 ml/min after a timeout of 30 seconds. Also, to stop bleeding of the ruptured blood vessel in the knee joint, the pressure in the joint is increased by a pressure control for the same time that flow is elevated. This pressure increase is predetermined in menu settings of the pump, and is in this example 40 mm Hg.

| Amount of blood in saline | Hb signal level | Trigger situation |
|---|---|---|
| 0 | 0 | Blood is not present |
| 0.05% | 10% | Blood is not present |
| 0.1% | 20% | Blood is present |
| 0.15% | 30% | Blood is present |
| 0.2% | 40% | Much blood is present |
| 0.25% | 50% | Much blood is present |
| >0.3% | Over range | Much blood is present |

For debris detection, the signal from the aforementioned optical IR sensor is used to detect the light absorbance of the liquid emerging from the knee. As debris originates as a result of the surgical process it will increases light absorption. The detection is formed by initially detecting and storing the signal from above described IR sensor; comprising the 875 nm LED and the photo detector. The liquid is clear and thus has a minimum absorbance. These first signal levels from both sensors are established during the start up of a procedure. Having established this first signal level, it is constantly compared to the signal during further use of the pump system during the procedure. As a trigger level of light absorbance is reached, the system considers debris present. This trigger level is established in vitro with a calibration liquid that is composed by boiling 1 dl of rice in 1 liter of water for 1 hour. This boiling liquid is then whipped and stirred for consistency in opacity.

The blood vessel adjacent to the optical detector in the outflow path may be smudged with body fats as a result of the surgical process. The signal processing compensates for this slow build up of offset of signal from the optical detector by periodically determining the smallest baseline value, and reestablishing this value as the new baseline value.

As debris is detected, the system identifies the situation reacts by increasing the flow of the aspiration pump to a higher level to rinse the knee. This higher level is preselected in the menu of the pump system, and is in this case 300 ml/min. When the debris detection determines that the increased flow has rinsed the knee as the signal level has returned to a low level, the aspiration pump returns to the intrinsic flow of 150 ml/min.

Rinsing of the knee may be initiated manually by the press of a button or a foot operated switch, and results in an increased liquid flow. However the detection of blood or debris as described above, automatically initiates the rinsing process.

Example 2

Detached Sensors

Figure 14:
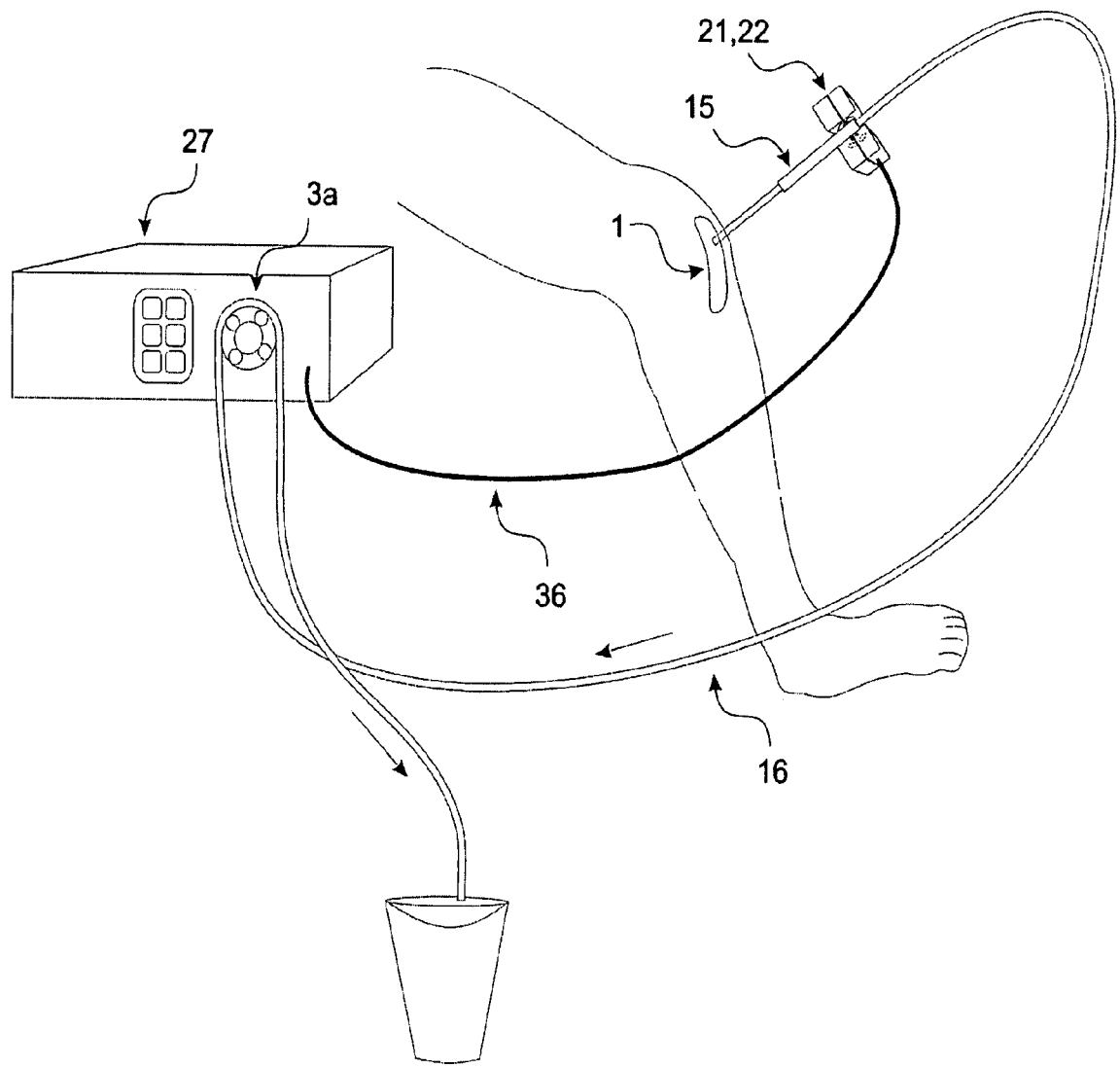
FIG. 14 shows an example of detached optical sensors

Fitting the optical sensors (21, 22) on a blood vessel near to, directly adjacent to the surgical instrumentation, or even within the surgical instrumentation is advantageous, as the reaction time as the debris and/or blood leaves the surgical site and as it reaches the optical sensors is reduced. This can be accomplished by use of a cable or wireless detector and a battery operated detector with wireless data transfer. The detector can be fitted on the cannula where the liquid normally is withdrawn from the surgical site as shown in the example in FIG. 14. In this example, wires (36) are used to connect the sensors to the operating control device (27). If the detector is fitted on or within the housing of a shaver, the wiring for the optical detector may be enclosed in the cable for the shaver.

Example 3

Detached Sensing

Figure 15:
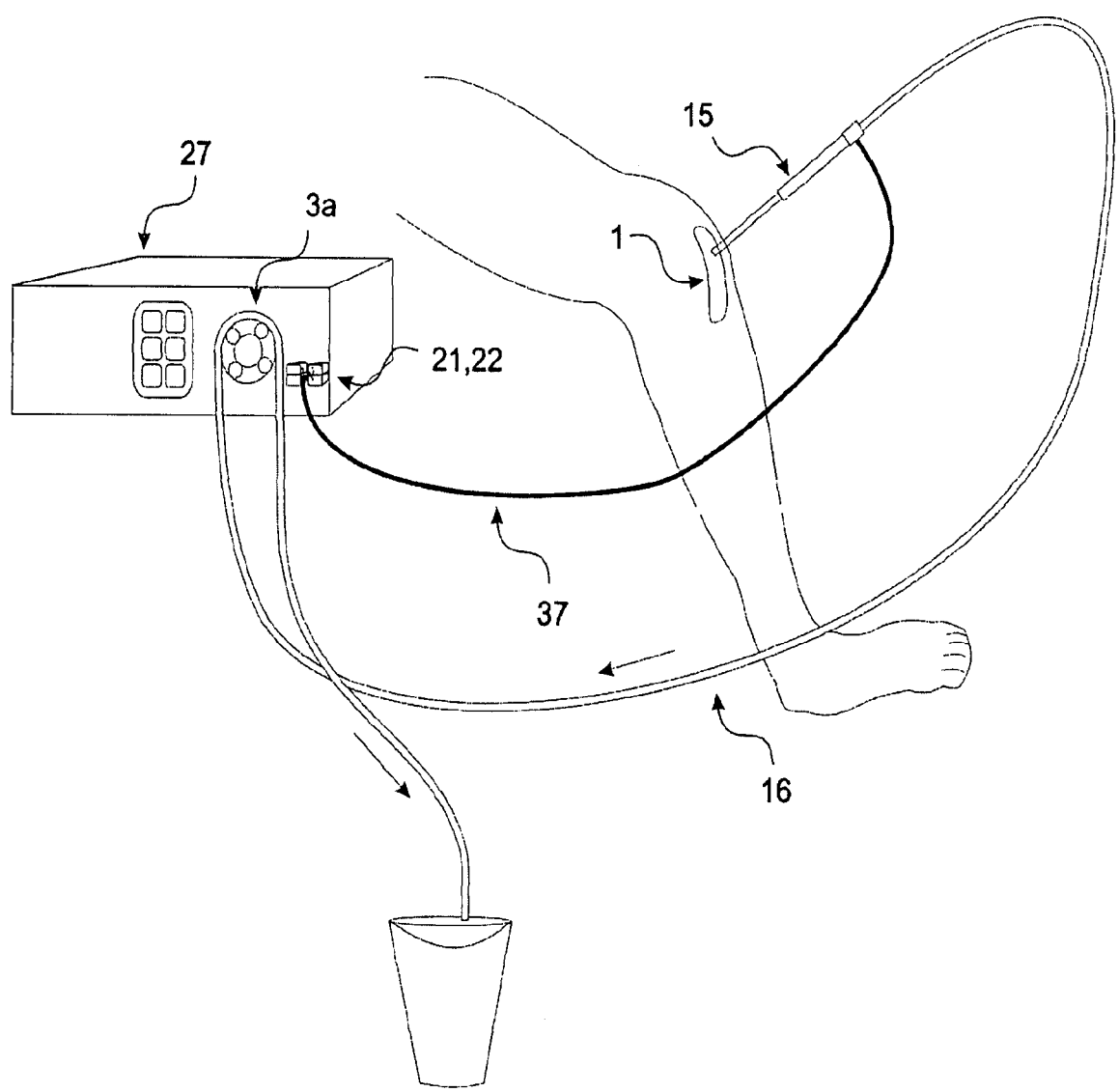
FIG. 15 shows an example of detached optical sensing

As shown in the example in FIG. 15, the optical sensors (21, 22) can be fitted in the operating control device (27), but the detection is made within the surgical instrumentation. Instead of electrically connecting the optical sensors to the operating control device (27), they are optically be connected to the surgical instrumentation by use of optical fibres (37).

Example 4

Accumulation of Hemoglobin Values

The signal values from the hemoglobin detection in Examples 1-3 and 5, are periodically accumulated in the memory of the processor or in another electronic memory. These accumulated values form a sum of signals values throughout the surgical process. This sum can be multiplied by a calibration factor, and thus be indicative of the amount of blood that has emerged from the patient as a result of the surgical process. This amount of lost blood can be displayed on the instrument display. Furthermore this blood loss can trigger an alarm to the operator, when the detected blood loss has reached a predetermined level.

Example 5

Smart Vision/Video

Below is an example of a technique to detect and distinguish blood and debris in the liquid inside a shoulder joint during an arthroscopic procedure using an irrigation system for body cavities. Signals from this detection are used to control the pressure in, and liquid flow through the shoulder joint in a manner that keeps it clear from blood and debris for good viewing with the arthroscope. If debris is detected, the flow through the shoulder joint is automatically elevated to efficiently rinse it. If blood is detected, the pressure is also automatically elevated, to inhibit blood to leave the broken vessels, by overcoming the blood pressure.

Figure 9:
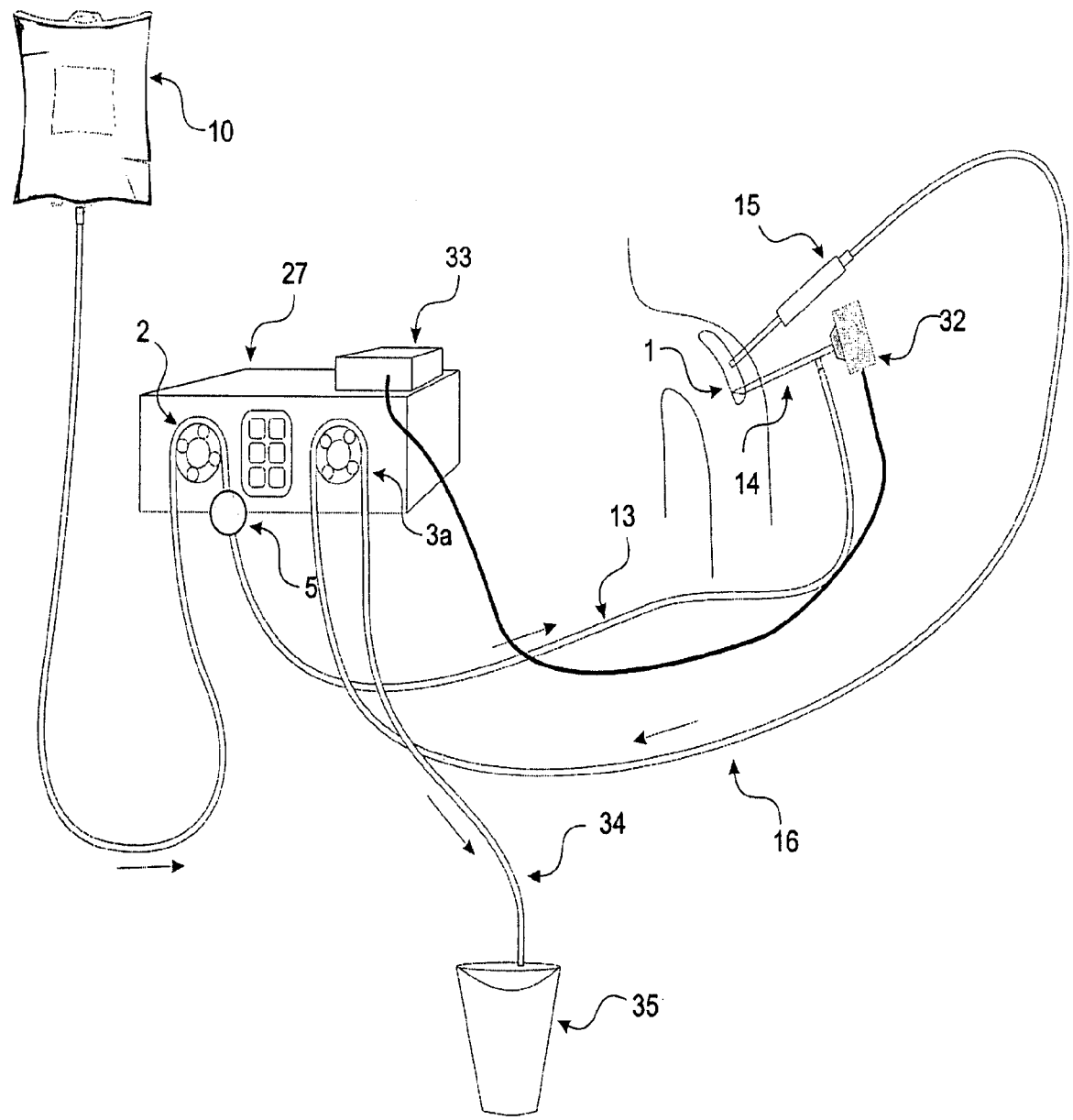
FIG. 9 shows a example of second embodiment of optical sensing

The setup is illustrated in FIG. 9. The system comprises a operating control device (27), a saline bag (10), connected to the inflow liquid pump (2) that pressurizes the feed line (13) by use of the pressure sensor (5) as described above. Liquid is trapped between the rollers of the inflow liquid pump (2), feed line (13), the arthroscope (14) with video camera (32), the body cavity, in this example a body cavity (1) in a shoulder, and further downstream: the instrument, in this case a shaver (15), outflow tubing (16), and the roller pumps of the outflow pump (3a). During flow in this closed liquid volume, the pressure drops all the way from the inflow liquid pump (2), to the outflow pump (3a). A video signal processor is illustrated as (33).

The detection of hemoglobin is obtained by use of the light reflected from the hemoglobin in the blood in the joint. The light reflected is that which is radiated by a light source (not illustrated) known in the art of endoscopy. The light is introduced in a designated channel in the arthroscope that is introduced in the shoulder. The reflection of this white light is detected by the photo sensitive video camera (32) fitted on the eyepiece of the arthroscope. The video signal output from the camera (32) is connected to a video signal processor (33). This functions for example in the following way.

The video signal is composed of a separate red, a blue and a green video signal component that combined composes the video color information. The video signal from the camera is fed to the signal processor (33) that divides every video line signal into 0.64 microsecond time slots. This corresponds to 100 time slots for every video signal line, where a picture frame is made up of 625 lines (PAL). The signal levels of red, blue and green are nearly the same for the images common in the view field of the arthroscope, meaning that it is generally ranging from white to black. If the signal level of red is >20% of either the blue or green during a time slot, a score of one is registered in a first frame memory in the signal processor. If the whole image is red, 62,500 score points would be registered. Every picture frame has its own score. The first frame memory in the signal processor has a rolling register function that has the capacity of score points from 10 frames. It is updated as every frame is completed and delivered by the camera. At every new frame the score value of the oldest frame is discarded. A score sum for the ten frames is calculated every time a new frame is delivered by the camera, thus introducing an averaging function.

If, during a period of 10 frames, the score sum is >30,000, blood is considered present, and if the score sum is >70,000, much blood is considered present.

If the score sum is >30,000 the video signal processor (33) will signal to the operating control device (27) which will react by increasing the flow of the aspiration pump to a higher level to rinse the shoulder. This higher level is preselected in the menu of the pump system, and is in this case 300 ml/min. If the score sum is >70,000, the flow will increase to 450 ml/min. When the blood detection determines that the increased flow has rinsed the shoulder as the signal level has returned to a low level, the aspiration pump (3a) will return to the intrinsic flow of 150 ml/min after a timeout of 30 seconds. Also, to stop bleeding of the ruptured blood vessel in the shoulder joint, the pressure in the joint is increased by a pressure control for the same time that flow is elevated. This pressure increase is predetermined in menu settings of the pump, and is in this example 40 mm Hg. Also other picture analysis techniques as known in the art could be used.

To detect debris, the signal processor (33) divides every video frame into 128×128 pixel elements. Every such pixel has a signal level that corresponds to the whiteness of the object that is visualized by the camera. This whiteness is nearly the same from video image frame to video image frame. The signal processor stores a value from 0 to 15 as this intensity value of the video signal of each pixel in a second frame memory. The pixel values are stored in a matrix fashion for each video image frame 25 consecutive frame matrixes are stored. This second memory in the signal processor has a rolling register function that rolls the 25 frames in a first in-first out fashion. It is updated as every video image frame is completed and delivered by the camera. As a new frame has developed by the camera, the oldest frame is discarded. A variation in the pattern in the second stored matrix is detected by the signal processing unit. This variation is identified as pixel intensities that are recognized as moving from one adjacent pixel to another in an identifiable fashion. As every pixel has a location in the matrix that corresponds to the physical image, a movement of intensity in the matrix location from image frame to image frame is a movement in relation to the surrounding, of a single object, in this case debris that float in the shoulder joint. Movement can be in any direction in the matrix. If 10 such movements are detected during one frame, a first score value is incremented by one in a memory cell representing a first score value. This score value is increment for each detection, and is decremented down to 0 for every frame there is no such detection. If there are over 500 detections in one frame, the camera is moved, and no score values are given. Also other picture analysis techniques as known in the art could be used.

Every second a frame matrix is stored in a third frame memory. This memory also has a rolling register function that rolls the 25 frames in a first in-first out fashion. If predominant consistently low signal levels are occurring in the third frame memory, dark areas are identified. If these dark areas are elevated to consistent signal >25% level over a time of 5 seconds, homogeneous debris is identified as present in the shoulder joint. Such occurrence increases the value a second score value by 10. If there is no such occurrence, this second score value will be decremented by 10 down to 0.

If either the first or second score values are >50, debris is considered present, and the video signal processor (33) will signal to the operating control device (27) which will react by increasing the flow of the aspiration pump to a higher level to rinse the shoulder. This higher level is preselected in the menu of the pump system, and is in this case 300 ml/min. When the debris detection determines that the increased flow has rinsed the shoulder as the score value has returned to <50, the aspiration pump (3a) will return to the intrinsic flow of 150 ml/min after a timeout of 5 seconds, and both score values are reset.

Example 6

Indirect Pressure Measurement

Figure 10:
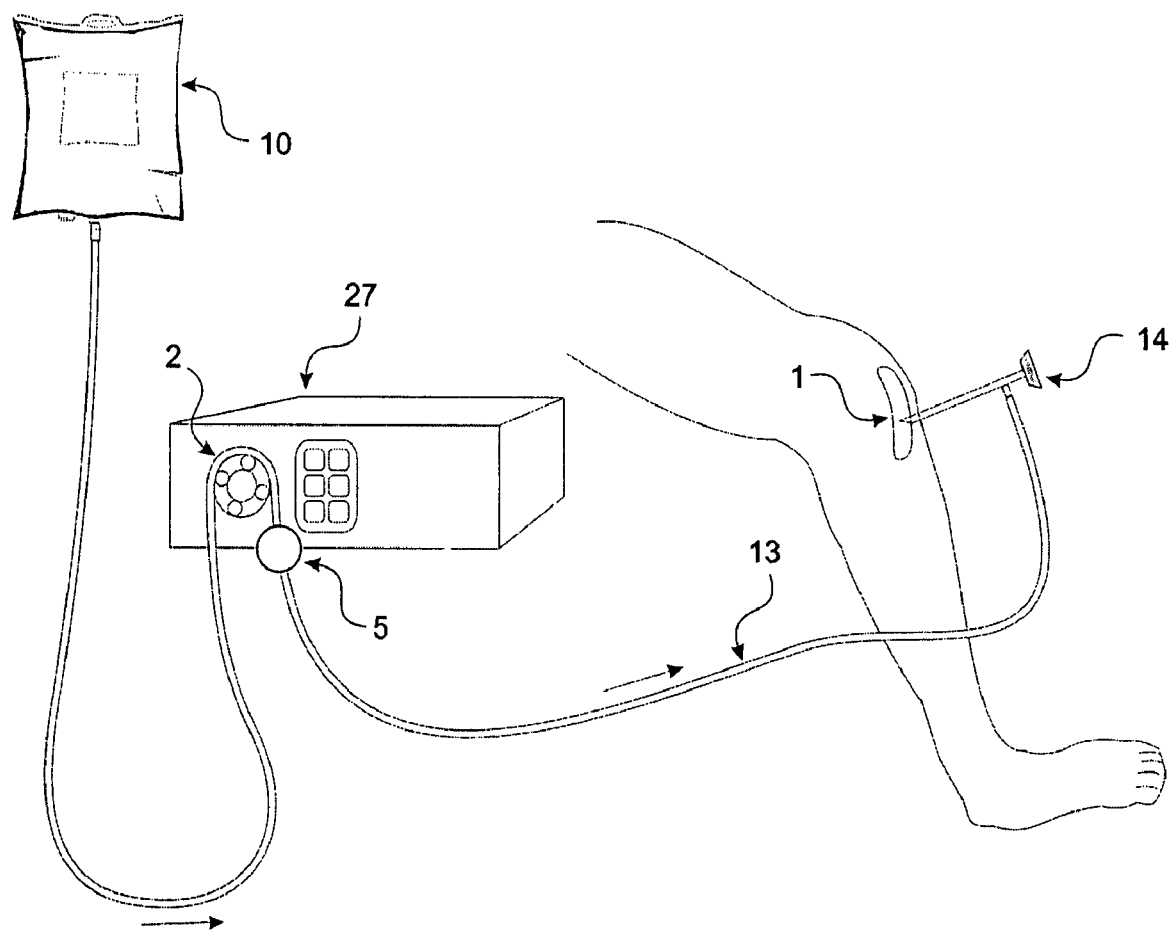
FIG. 10 shows the liquid inflow arrangement

As shown in FIG. 10, the operating control device (27) that manages the liquids to the surgical site comprises a peristaltic roller pump (2) known in the art of pumping liquids. The pump is a peristaltic roller type pump known in the art of pumping liquids. The pump model is SR 25, available from ASF Thomas, Industries GmbH, Siemensstrasse, 82178 Puchheim, Germany, and has a flow range of 0-740 ml/minute. It can pressurize the surgical site—in this example a body cavity (1) in a knee—up to 200 mm Hg. The pump, further referred to as the inflow liquid pump, transports the irrigation liquid from saline bags (10) into the knee. The pump pressurizes the liquid in the downstream tubing (13) and in a liquid dome with a flexible membrane for a pressure sensor (5). The pressure sensor is known in the art of measuring arterial blood pressure in an invasive fashion, and is a Hewlett Packard 1290C from Sorensen Research, 4455 Aetherton Drive, Salt Lake City, Utah 84123-2584, USA. The pressure sensor is flush mounted in the front panel of the pump. The signals from the pressure sensor are amplified and fed to an A/D converter, which is giving signals to the microcontroller of the operating control device (27). The measured pressure is compared to a desired first controlled pressure. This first controlled pressure is servo controlled by the microcontroller in the operating control device (27) to maintain pressure by controlling the frequency of steps to the pump motor. This first controlled pressure is thus the result pressure in the pressure sensor (5), and is further in this example referred to as inflow irrigation liquid pressure.

The pressurized liquid is then fed by the downstream tubing (13) from the dome into the knee via the arthroscope (14).

Figure 13:
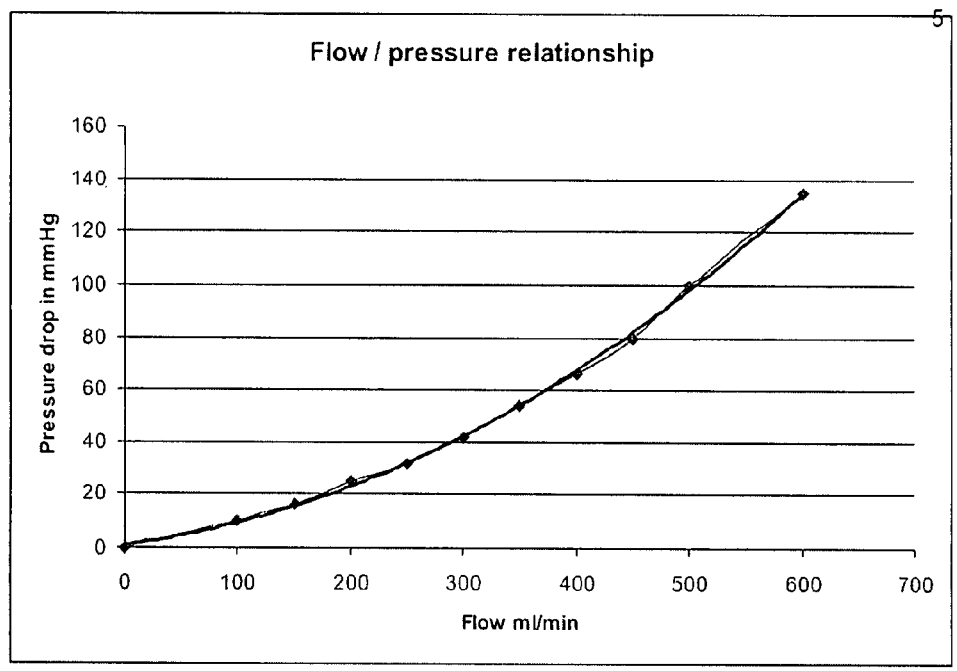
FIG. 13 shows an example of a flow/pressure drop relationship diagram

If there is a flow, the pressure in the knee will be lower than that in the dome. The reason is that there is a pressure loss in the tubing from the pump, and the arthroscope; due to the hydraulic resistance of the tubing and arthroscope. The higher flow into the knee, the more the pressure drops. The pressure drop in mm Hg can be described as flow2*0.0003+ flow*0.0523, where the flow is expressed in ml/min. See FIG. 13.

The desired pressure in the knee is set in the user menu of the system. This has a default value of 120 mm Hg. To achieve this pressure in the knee, the pressure that the inflow liquid pump produces must compensate for the resistance as above. The operating control device takes this resistance into account when calculating the inflow irrigation liquid pressure to correspond to the pressure in the knee. At the intrinsic flow value of 150 ml/min, the inflow irrigation liquid pressure will be set to 135 mm Hg by the operating control device. At 300 ml/min, the inflow irrigation liquid pressure is set to 155 mm Hg by the operating control device. This processing provides good control over the actual pressure in the knee.

Figure 11:
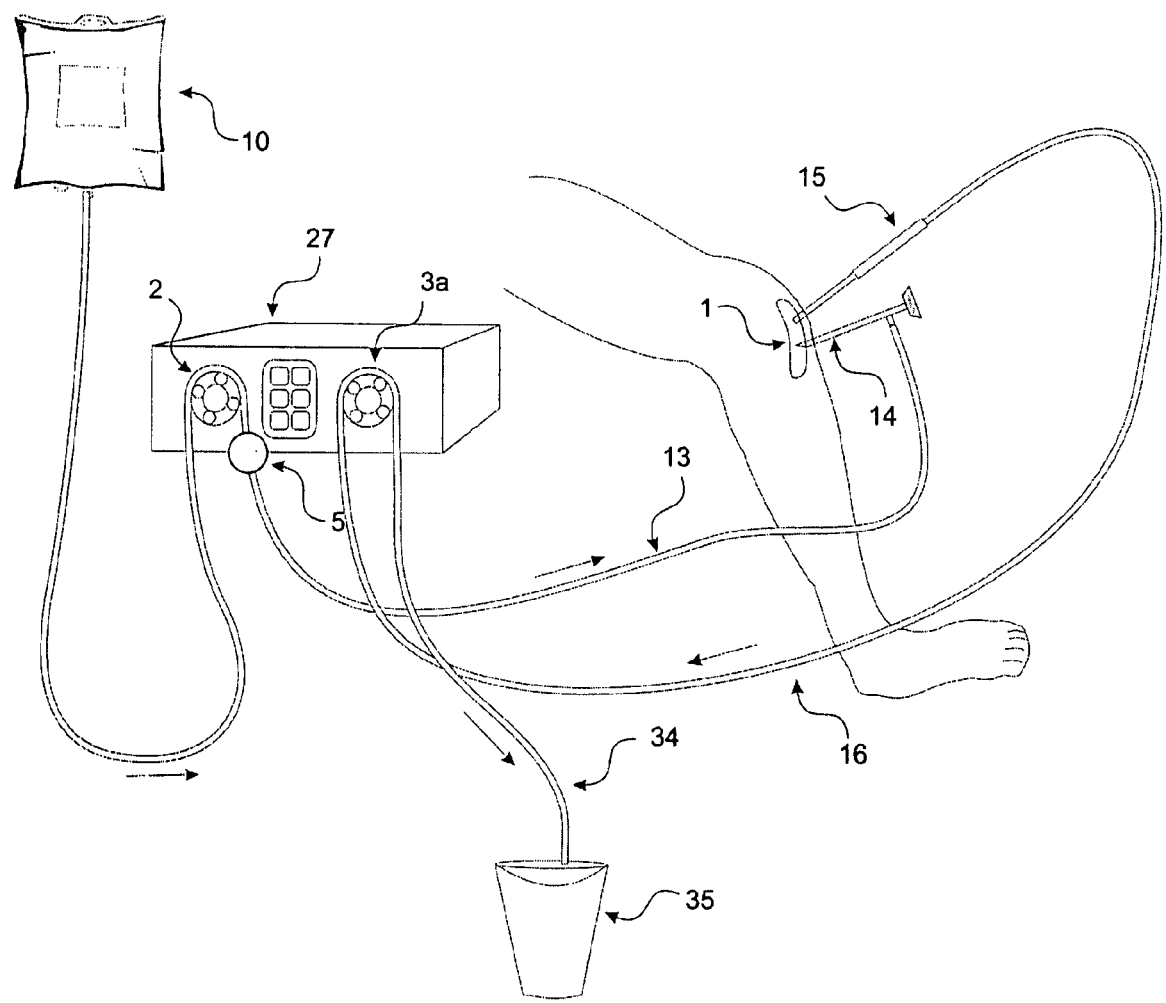
FIG. 11 shows an example of outflow tracking

The complete setup is illustrated in FIG. 11. The system comprises a operating control device (27), a saline bag (10), connected to the inflow liquid pump (2) that pressurizes the feed line (13) by use of the pressure sensor (15) as described above. Liquid is trapped between the rollers of the inflow liquid pump (2), feed line (13), the arthroscope (14), the surgical site, in this example a body cavity (1) in a knee, and further downstream: the outflow instrument (15) in this case a cannula port, outflow tubing (16), and the roller pumps of the outflow pump (3a). During flow in this closed liquid volume, the pressure drops all the way from the inflow liquid pump (2), to the outflow pump (3a).

The pressure drop described above only occurs when there is a flow. The law of communicating vessels teaches us that the pressure is the same in the entire feed line when the flow is 0. The system takes advantage of this and stops the inflow liquid pump and aspiration pump every 5 minutes. At that instant, the flow begins to diminish, and after 2 seconds it is 0. The inflow irrigation liquid pressure confirms the pressure calculation, as the inflow irrigation liquid pressure is now the same as the pressure was in the knee. If there is an error, the flow/pressure relationship formula is accordingly adjusted in the operating control device. For instance, at the intrinsic flow value of 150 ml/min, the inflow irrigation liquid pressure will be set to 135 mm Hg by the operating control device to achieve 120 mmHg in the knee. As the pumps are stopped, the inflow irrigation liquid pressure 100 mmHg is measured after the stabilization time of 2 seconds. The set inflow irrigation liquid pressure will be adjusted by 120/100, namely ~20% higher; further on during this procedure. After the procedure, this pressure adjustment is not implemented.

Leakage is indicated by the invention as follows. If, during above mentioned stopping of the pumps to confirm indirect pressure measurement, the pressure is dropping, the hydraulic system has a leak in it. It is detected by the operating control device as it measures inflow irrigation liquid pressure during the stop time of the pumps, and awaits the stabilization of 2 seconds. This leakage can be 100 mm Hg/min, causing an alarm to the operator, and stopping the pump. If the leakage is very abrupt such as 100 mm Hg/sec, there is a technical leakage such as a removed cannula or loosened tubing from the arthroscope. This causes a different alarm; also stopping the pump. Volume establishment, by keeping track of the number of pump motors turns, is in neither of these two leakage situations taken into account in the compliance measurement The flow generated is sometimes manually increased by the operator by use of panel controls. The reason for increasing flow may be as a user's intention to manually rinse the joint, or when a shaver instrument is used. It may also be an automatic increase when blood or debris is detected as described above. The time for reaching the new flow is reduced by giving the inflow an enhanced acceleration by overpressure as illustrated in FIG. 7. The acceleration is calculated as a derivate of the pressure. An ordinary pressure curve (Pnorm) illustrates the pressure over time, and a resulting flow (Qnorm). With a 2 second overpressure to 200 mmHg as illustrated with (Pnew), the flow increases as in (Qnew), resulting in a quicker target flow (Q2) ad target pressure (P2). This pressure overshooting is a yet another function in the system to gain good control over the pressure in, and flow through the knee.

The system can calculate the expansion of the knee as it is pressurized. The pressure and the volume figures give us the compliance value in ml/mmHg. Pressure is measured as described above, and the knee fill volume is the difference between the inflow and outflow, over time. The volumes are calculated by the microcontroller, as the number of turns the pump head makes. For instance at a knee pressure of 120 mm Hg, a fill volume of 60 ml is derived by difference in rotation of the inflow and outflow pumps. This difference is calculated when the tubing is empty of air and the knee begins to be pressurized, until the pressure is reached. As a second pressure of 150 mm Hg is introduced into the knee, the volume becomes 70 ml.

Compliance is calculated as $$C = \frac{V_{1cavity} - V_{2cavity}}{P_{1cavity} - P_{2cavity}}$$

where the V1cavity is the first volume in the body cavity, and V2cavity is a second volume in the body cavity. P1cavity is a first pressure in the body cavity and P2cavity is a second pressure in the body cavity. In this example the compliance is thus $$C = \frac{70 - 60}{150 - 120} = 0.33 \text{ ml/mmHg}$$

This compliance value is stored in the memory of the microprocessor in the operating control device. The compliance value is displayed in the system display. Also, if the compliance value exceeds 0.5 ml/mm g, an audio alarm is triggered and the pump is stopped. Physiologically, this is a warning that tissue damage has passed a safe level, and excessive amounts of liquid may leave the knee in the surrounding tissue.

Example 7

Outflow Tracking in a Knee Application

The complete setup is illustrated in FIG. 11. The system comprises a operating control device (27), a saline bag (10), connected to the inflow liquid pump (2) that pressurizes the feed line (13) by use of the pressure sensor dome (5) as described above. Liquid is trapped between the rollers of the inflow liquid pump (2), feed line (13), the arthroscope (14), the surgical site, in this case a body cavity (1) in a knee joint, and further downstream: a shaver instrument (15), outflow tubing (16), and the roller pumps of the outflow pump (3a). Liquid is then disposed of through outflow tubing (34) into waste bucket (35).

The microcontroller in the operating control device (27) controls the rotational speed of the stepper motors for the pumps. Each step the motor makes, represent a small displaced volume.

As the knee initially in the surgical procedure is pressurized with the inflow liquid pump (2), the distension volume increases and the knee joint will expand. The expansion is approximately 90 ml in this example. Pressure is 100 mm Hg.

Figure 12:
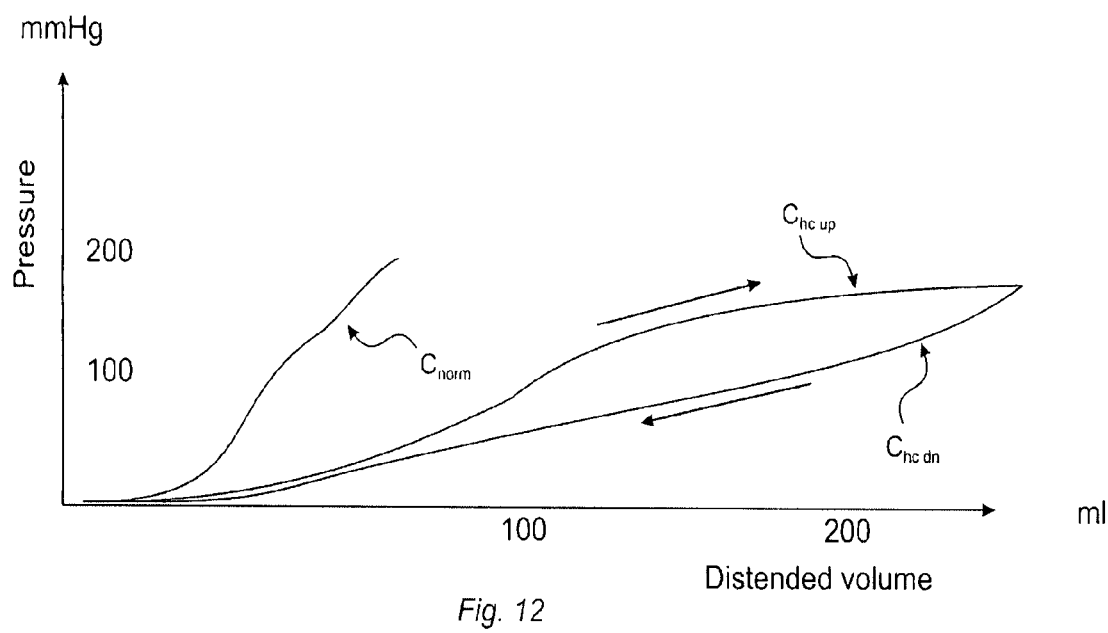
FIG. 12 shows an example of a joint pressure/volume diagram

FIG. 12 illustrates a pressure/distended volume curve (Cnorm) for a normal characteristic joint such as a knee. The higher pressure, the more the joint is filled with liquid. As a shoulder has a higher compliance, pressurization causes a bigger distension volume. The curve (Chc up) illustrates this, as the shoulder is pressurized (goes up). The distension volume is increased to 200 ml at a pressure of 160 mm Hg in our example. When releasing pressure, volume will diminish as illustrated in curve (Chc dn) (goes down). This illustrates tissue hysteresis as the volume to some extent persists as the pressure drops.

The pressure is controlled in the shoulder joint by the pressure control for the inflow liquid pump. As noted, a fairly small increase in pressure may result in a large volume increase.

When the shaver instrument is used, the liquid in the shoulder is rapidly evacuated, as the outflow pump speeds up to evacuate debris via the shaver instrument tool. At that time the outflow will be 300 ml/min. A significant liquid evacuation will occur, but the pressure will only drop a little, and this drop is even smaller at the measuring point for it—namely the pressure sensor dome—due to the hydraulic resistance between the shoulder and the pressure dome. This would result in reduced vision as the shoulder joint collapses. However, this process of the system beneficially locks the inflow liquid pump speed to that of the outflow rotation speed to thus replace the evacuated liquid with the same amount that the outflow pump evacuates. This eliminates the problem of a collapsing shoulder.

The invention claimed is:

1. A pressure regulation method of an irrigation liquid at a surgical site in a body cavity (1), in which method an inflow liquid pump (2) pressurizes the irrigation liquid in a feed line (13) and in which an outflow device (3) drains the irrigation liquid from the body cavity (1) through a tubing (16) and in which a control unit (4) controls both the inflow liquid pump (2) and the outflow device (3) depending on an inflow irrigation liquid pressure from a pressure sensor (5), characterized in that the control unit (4) compares the inflow irrigation liquid pressure and flow values with pressures calculated to correspond to pressures in the body cavity for the respective flow, and that alignment between the pressure values is made by altering the effect of the inflow liquid pump (2) and/or the outflow liquid device (3), the method further characterized in that the inflow irrigation liquid pressure depends on detected and registered signals from optical sensors (21,22) provided at the tubing (16) on the outflow site of the body cavity (1), the optical sensors comprising a first optical sensor and a second optical sensor, the method further utilizing a debris identification module (25) for registering the amount of debris in the liquid coming out from the surgical site and a separate blood identification module (26) for registering the amount of blood cells, red blood cells, and/or haemoglobin, wherein each of the identification modules is provided for cooperation with one or both of the sensors (21, 22), and wherein the method further comprises utilizing a second control unit (24) that increases the effect of the inflow and/or outflow liquid pump (3a) to rinse the surgical site until a level of clear vision in the module is reached so that the control unit (4) automatically increases the flow of the inflow irrigation liquid when the amount of debris is increased in the irrigation liquid in, or coming out of, the surgical site or regulates the pump so that the pressure of the irrigation liquid is increased when the amount of blood or haemoglobin is increased in or coming out of the surgical site.

2. The method according to claim 1, wherein the outflow device (3) is either an outflow liquid pump (3a) or an outflow shut off valve (3b) or a combination of an outflow shut off valve (3b) and an external suction source (3c).

3. The method according to claim 2, further comprising providing a recalculation device in the control unit (4) together with a calibration device for the pressure from the pressure sensor (5) and flow values for recalculating the inflow irrigation liquid pressure and the flow comparison for an actual surgical site by simultaneously stopping both the inflow liquid pump (2) and the outflow liquid pump (3a) or alternatively stopping the inflow pump (2) and the outflow liquid with a outflow shut off valve (3b), during a time interval, and continuously registering the inflow irrigation liquid pressure of the pressure drop in the liquid volume between both pumps or between the inflow pump (2) and the shut off valve (3b) during the time interval.

4. The method according to any of the claims 1-3, wherein the optical sensors (21, 22) register the blood cells, the red blood cells, the haemoglobin and/or the amount of debris in the liquid coming out from the surgical site and compare these registered values with reference values in the second control unit (24).

5. The method according to claim 4, wherein the optical sensors (21,22) comprise a light emitting diode and a photo detector.

6. The method according to claim 4, wherein the optical sensors (21,22) comprise a video camera and a video signal processor, and wherein the video camera can be attached on a surgical instrument, on a separate optical fiber or at the tubing on the outflow site of the surgical site.

7. The method according to claim 1, wherein a change in flow is made automatically by the pump or manually by the operator, such change of flow being made in a manner compensating for reactance in the tubing and instrumentation.

* * * * *